(12) United States Patent
Maruyama

(10) Patent No.: US 11,583,184 B2
(45) Date of Patent: Feb. 21, 2023

(54) MEDICAL OPTICAL IMAGING DEVICE

(71) Applicant: THE YOSHIDA DENTAL MFG. CO., LTD., Tokyo (JP)

(72) Inventor: Naoki Maruyama, Tokyo (JP)

(73) Assignee: THE YOSHIDA DENTAL MFG. CO., LTD., Tokyo (JP)

( * ) Notice: Subject to any disclaimer, the term of this patent is extended or adjusted under 35 U.S.C. 154(b) by 0 days.

(21) Appl. No.: 17/761,624

(22) PCT Filed: Aug. 5, 2020

(86) PCT No.: PCT/JP2020/030052
§ 371 (c)(1),
(2) Date: Mar. 18, 2022

(87) PCT Pub. No.: WO2021/053990
PCT Pub. Date: Mar. 25, 2021

(65) Prior Publication Data
US 2022/0330824 A1    Oct. 20, 2022

(30) Foreign Application Priority Data
Sep. 20, 2019    (JP) .............................. JP2019-172349

(51) Int. Cl.
*A61B 5/00*        (2006.01)
*A61B 1/06*        (2006.01)
(Continued)

(52) U.S. Cl.
CPC .......... *A61B 5/0066* (2013.01); *A61B 1/0605* (2022.02); *A61B 1/24* (2013.01); *A61B 6/463* (2013.01)

(58) Field of Classification Search
None
See application file for complete search history.

(56) References Cited

U.S. PATENT DOCUMENTS

2002/0109912 A1    8/2002   Knoblich
2003/0107652 A1    6/2003   Williams
(Continued)

FOREIGN PATENT DOCUMENTS

JP    2005-80734 A    3/2005
JP    2005-152569 A    6/2005
(Continued)

OTHER PUBLICATIONS

International Search Report and Written Opinion dated Sep. 15, 2020 corresponding to International Patent Application No. PCT/JP2020/030052, with partial English translation thereof.
(Continued)

*Primary Examiner* — Clifford Hilaire
(74) *Attorney, Agent, or Firm* — Squire Patton Boggs (US) LLP

(57) ABSTRACT

The present invention addresses the problem of providing a small-sized, low-cost medical optical imaging device capable of irradiating even a deep portion of a dental root canal. Provided is a medical optical imaging device (4) that is provided with an illumination unit (6) for emitting illumination light to a subject, an imaging section (7) for imaging the subject, and a controller (8) for controlling at least the imaging section (7). The imaging section (7) is provided with an imaging lens system (71) and an imaging element (72) for receiving an optical image created by the imaging lens system (71). When viewed from the subject side, the illumination unit (6) is disposed in front of the imaging lens system (71) and overlapping the imaging lens system (71).

13 Claims, 16 Drawing Sheets

(51) Int. Cl.
*A61B 1/24* (2006.01)
*A61B 6/00* (2006.01)

(56) References Cited

U.S. PATENT DOCUMENTS

| | | |
|---|---|---|
| 2006/0028719 A1 | 2/2006 | Kaneko et al. |
| 2011/0058716 A1 | 3/2011 | Okawa et al. |
| 2011/0221878 A1* | 9/2011 | Kitaoka ............... A61B 1/0676 348/66 |
| 2015/0216418 A1* | 8/2015 | Ammon ................ A61B 1/24 433/29 |
| 2017/0311872 A1 | 11/2017 | Matsuda |
| 2020/0093363 A1* | 3/2020 | Saika ................... A61B 3/0025 |
| 2020/0146556 A1 | 5/2020 | Kim |

FOREIGN PATENT DOCUMENTS

| | | |
|---|---|---|
| JP | 2006218206 A | 8/2006 |
| JP | 2011-120882 A | 6/2011 |
| JP | 2011104186 A | 6/2011 |
| JP | 2017167222 A | 9/2017 |
| WO | WO 2009/148044 A1 | 12/2009 |
| WO | 2011023062 A1 | 3/2011 |
| WO | WO 2016/108276 A1 | 7/2016 |
| WO | 2019022361 A1 | 1/2019 |

OTHER PUBLICATIONS

Notice of Reasons for Refusal dated Oct. 26, 2020 corresponding to Japanese Patent Application No. 2020-544549 with English translation.
Decision to Grant a Patent dated Feb. 9, 2021 corresponding to Japanese Patent Application No. 2020-544549 with English translation.
Supplementary European Search Report issued in corresponding European Patent Application No. 20864455.9 dated Oct. 10, 2022.
Communication pursuant to Article 94(3) EPC issued in corresponding European Patent Application No. 20864455.9 dated Oct. 21, 2022.

* cited by examiner

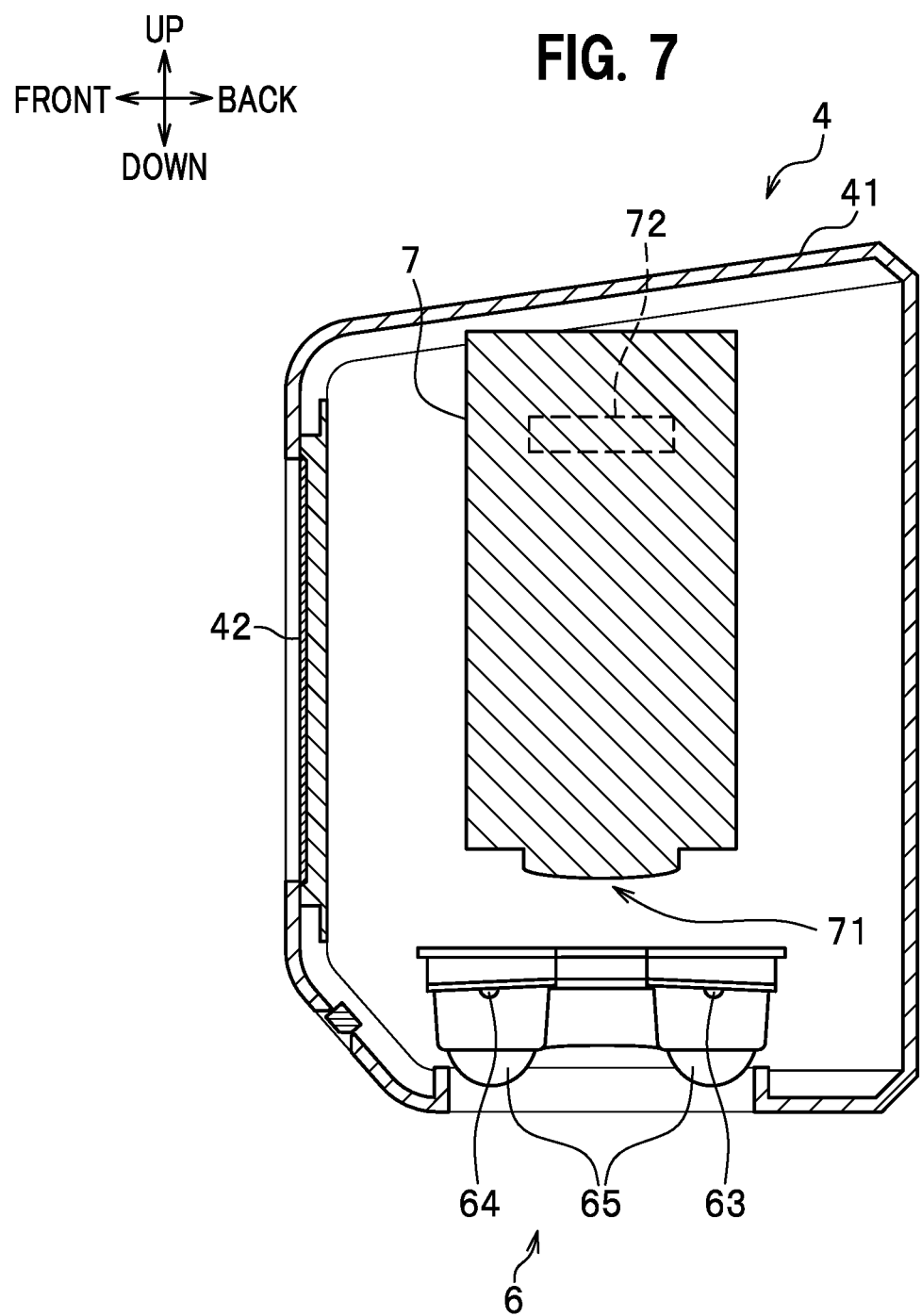

FIG. 10A
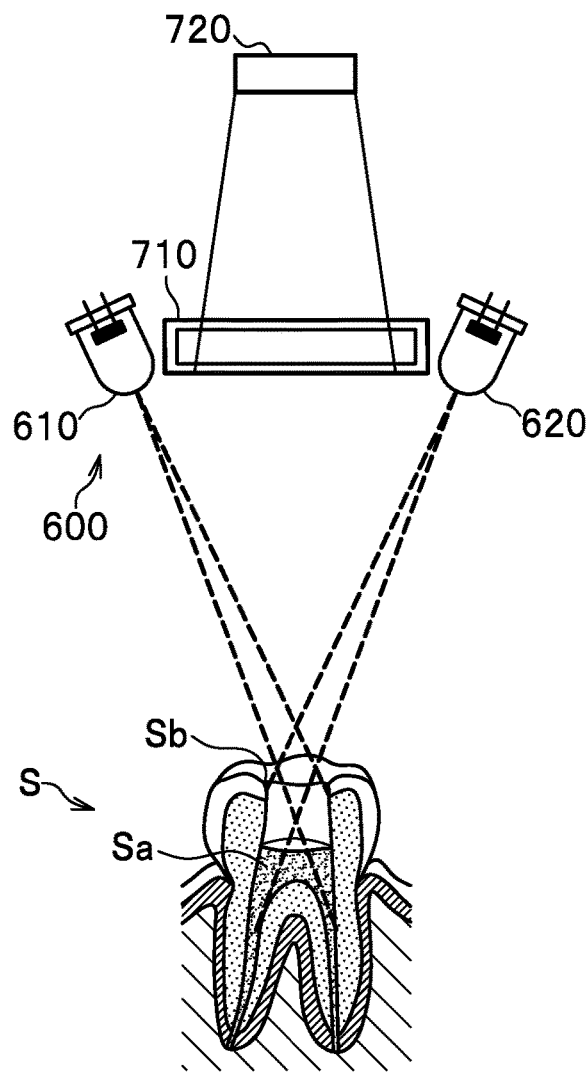
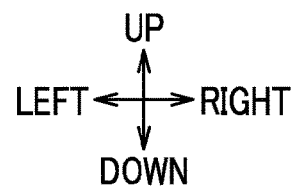
FIG. 10B
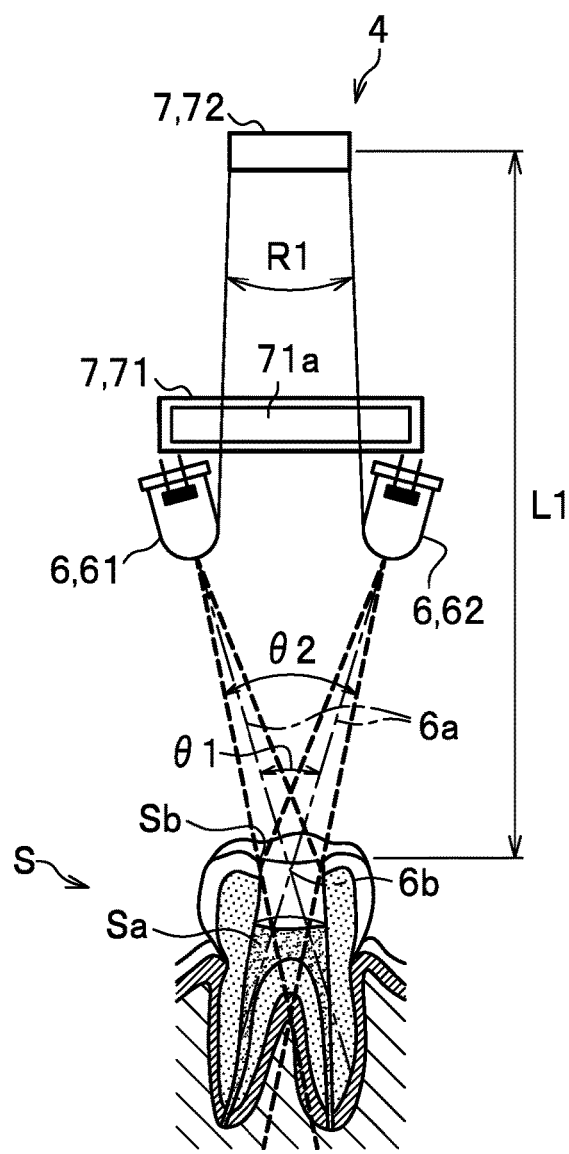
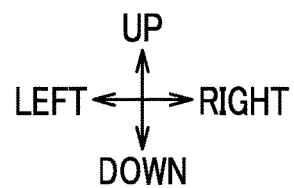

FIG. 11A
FIG. 11B
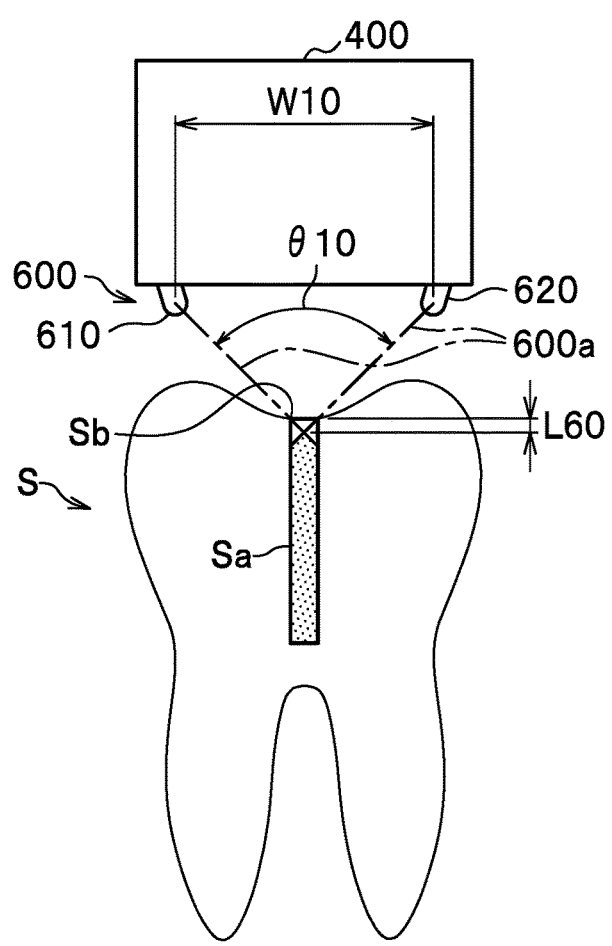
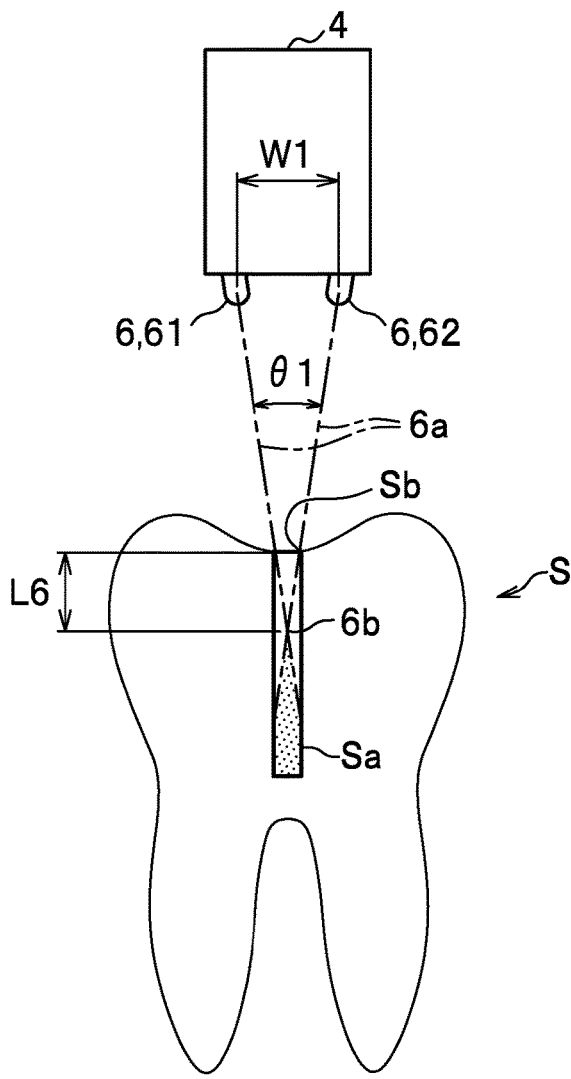
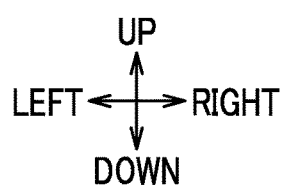
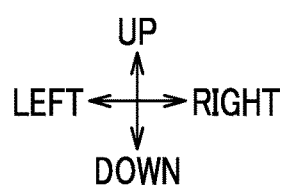

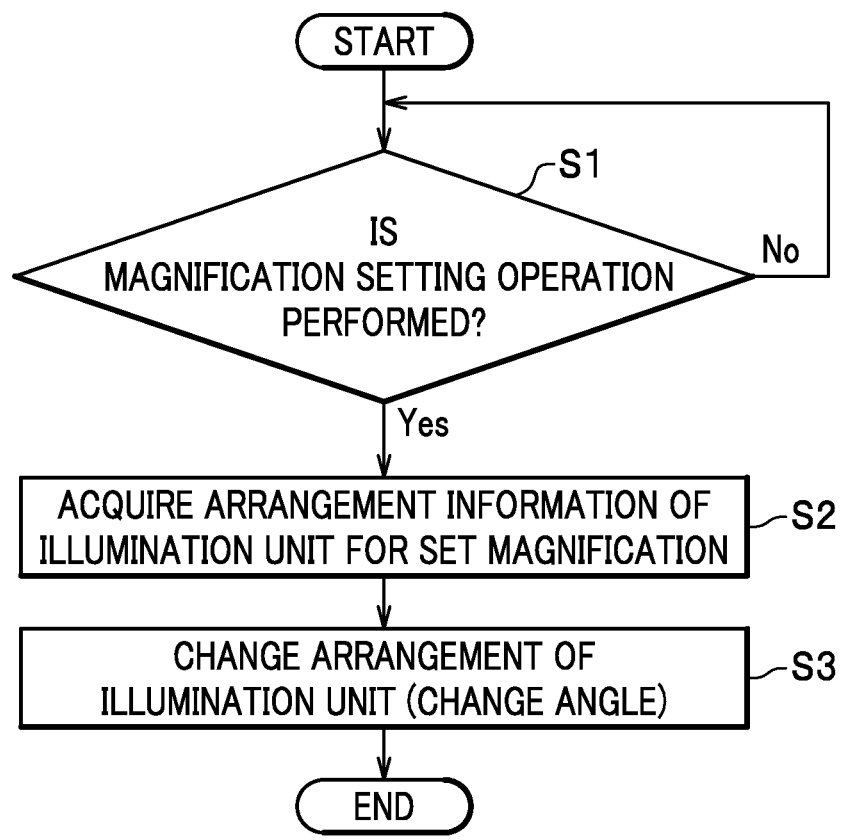

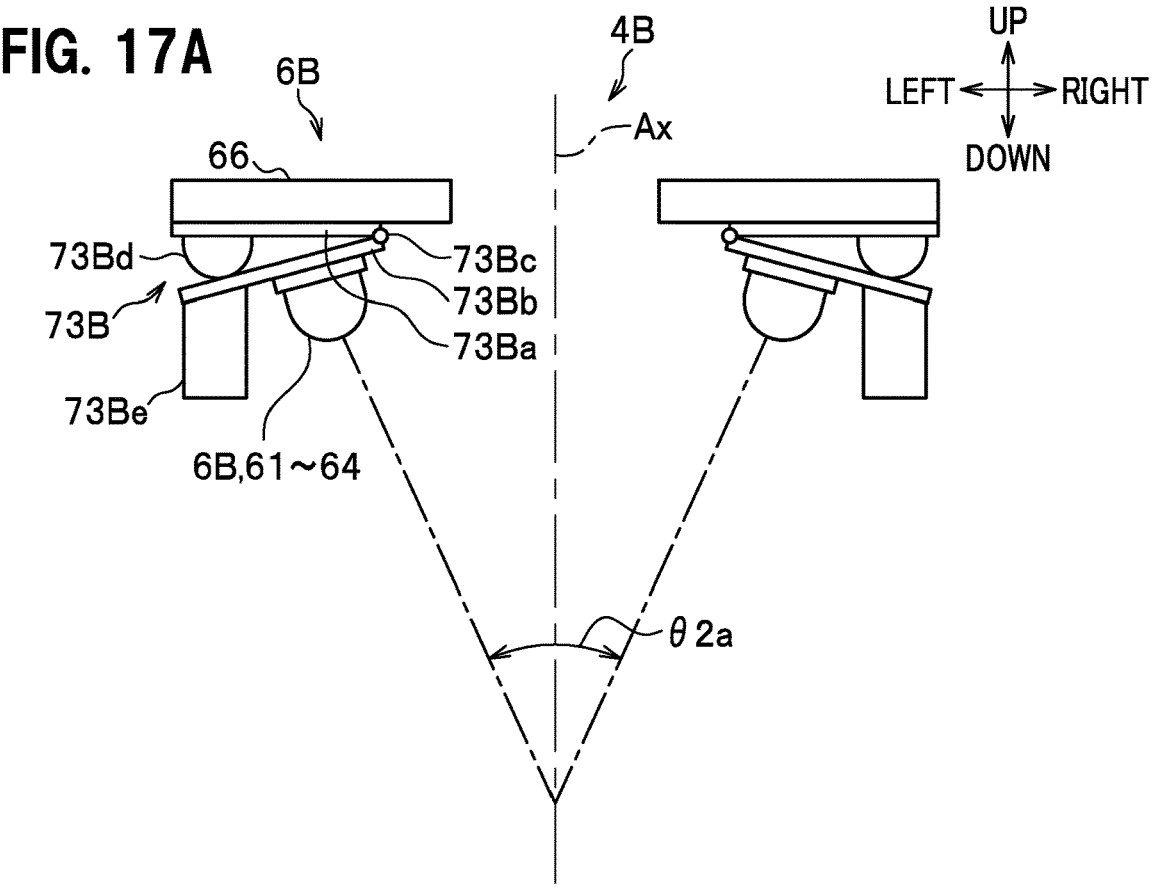
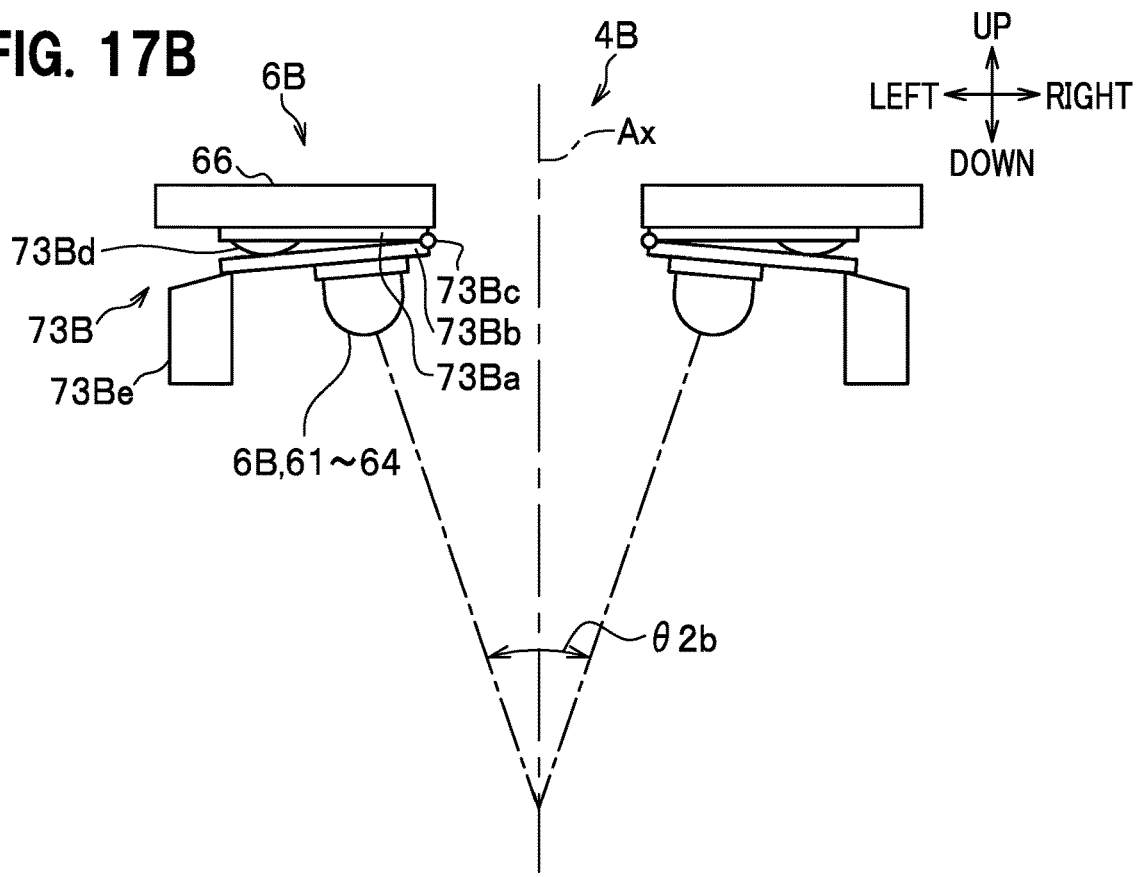

MEDICAL OPTICAL IMAGING DEVICE

TECHNICAL FIELD

The present invention relates to a medical optical imaging device.

BACKGROUND ART

Therapeutic procedures including surgeries or dental examinations using a dental examination system generally employ a microscope, an imaging device, and an illumination device for precise treatments and diagnoses.

Examples known as a dental examination system including an imaging device and an illumination device are an oral cavity observation apparatus for treatment and a dental treatment device described in Patent Literature 1 and a dental optical imaging device described in Patent Literature 2.

The oral cavity observation apparatus for treatment according to Patent Literature 1 employs coaxial illumination using the same axis to irradiate an observation site in an oral cavity with light emitted from a light source (11) and to capture images thereof, and a half mirror (10) is used for irradiation of the observation site.

In the dental optical imaging device according to Patent Literature 2, LED illumination devices (35, 36), as a target for above-described comparison, are arranged around the lens diagonally to an optical axis AX of an extraoral camera.

CITATION LIST

Patent Literature

Patent Literature 1: Japanese Patent Application Publication No. 2011-104186 (FIG. 1(a) to (d))

Patent Literature 2: WO2016/108276 (FIG. 3)

SUMMARY OF INVENTION

Technical Problem

In the oral cavity observation apparatus for treatment of Patent Literature 1, light from the light source (11) is transmitted through the half mirror (10) to be received by a camera system (13), and about fourfold illuminance is necessary compared to the LED illumination devices arranged around the lens. In addition, the oral cavity observation apparatus for treatment of Patent Literature 1 has problems that the need for virtual image formation and the half mirror (10) increases the body size and thereby increases the cost.

In the dental optical imaging device of Patent Literature 2, optical axes (AL-1, AL-2) of the LED illumination devices (35, 36) form a large angle therebetween. At illuminating a root canal, therefore, light does not reach deep into the root canal and forms a shadow, resulting in low visibility. In a treatment of drilling in a root canal, it is difficult to see the condition of the drilled part in the root canal.

An object of the present invention therefore is to provide a small-sized, inexpensive medical optical imaging device which is capable of illuminating deep in a root canal.

Solution to Problem

To solve the above problems, the present invention is a medical optical imaging device including: an illumination unit that emits illumination light toward a subject; an imaging section that images the subject; and a controller that controls at least the imaging section. The imaging section includes an imaging lens system and an imaging element that receives an optical image formed by the imaging element, and the illumination unit is located in front of the imaging lens system and overlaps the imaging lens system as viewed from the subject's side.

Advantageous Effects of Invention

According to the present invention, it is possible to provide a small-sized, inexpensive medical optical imaging device which is capable of illuminating deep in a root canal.

BRIEF DESCRIPTION OF DRAWINGS

FIG. 7 is a VII-VII cross-sectional view of FIG. 4.

FIG. 10A is an explanatory view illustrating an illumination unit of a comparative example.

FIG. 10B is an explanatory view illustrating the illumination units of the present invention.

FIG. 11A is an explanatory view illustrating optical axes of the illumination unit of the comparative example.

FIG. 11B is an explanatory view illustrating optical axes of the illumination units of the present invention.

FIG. 14 is a flowchart illustrating control to automatically change the arrangement of the illumination units without manual zooming.

FIGS. 17A and 17B are views illustrating a second modification of the medical optical imaging device according to the embodiment of the present invention, FIG. 17A being an explanatory view illustrating the state of the illumination units for a small magnification, FIG. 17B being an explanatory view illustrating the state of the illumination units for a large magnification.

DESCRIPTION OF EMBODIMENTS

Figure 1:
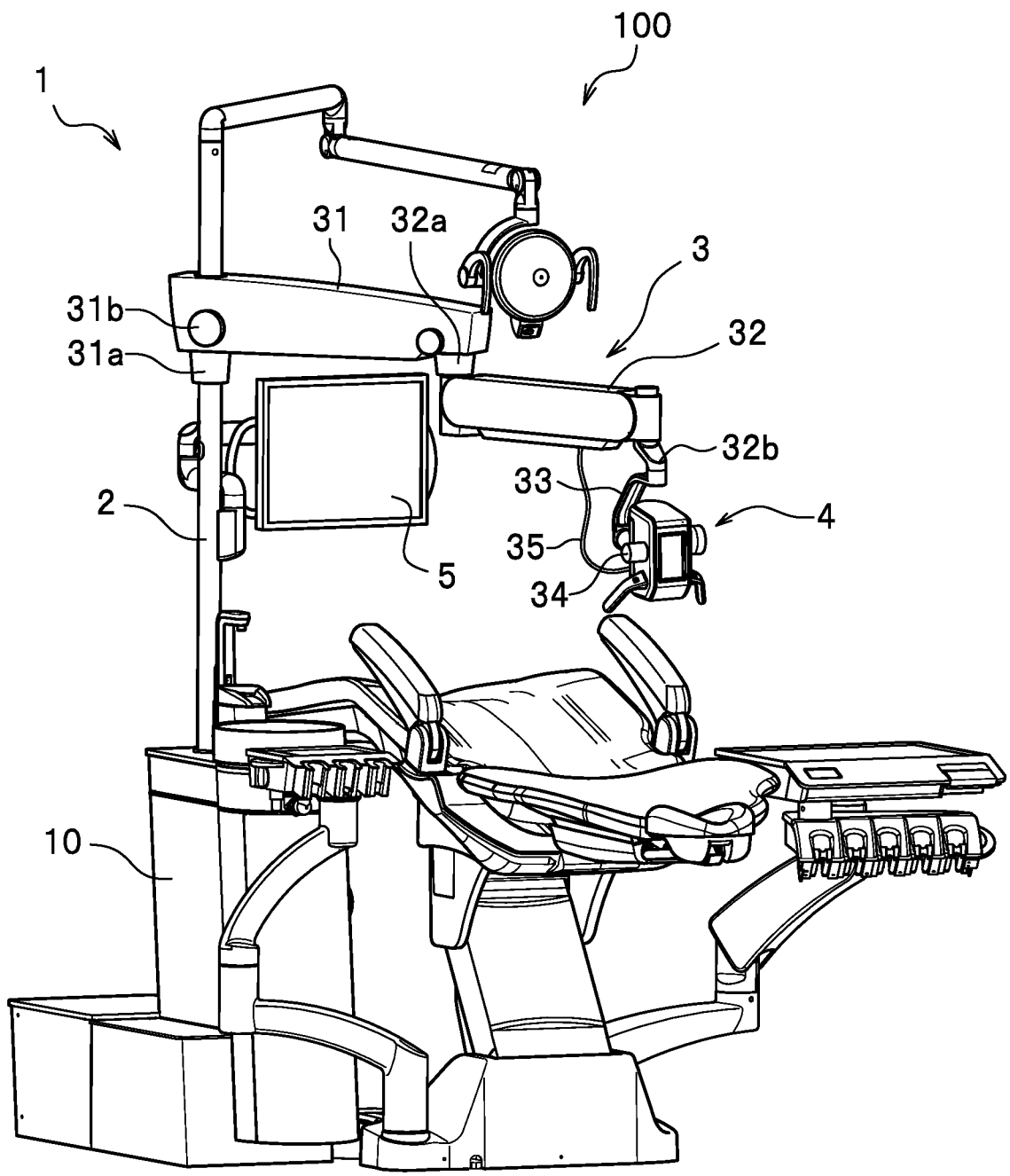
FIG. 1 is a perspective view illustrating a medical optical imaging device example according to an embodiment of the present invention.

Next, a medical optical imaging device (hereinafter, conveniently referred to as an "imaging device 4") according to an embodiment of the present invention will be described with reference to FIGS. 1 to 15. Prior to description of the imaging device 4, a medical examination apparatus 100 on which the imaging device 4 is mounted will be described first.

The embodiment will be described such that illustrations in FIGS. 3 and 4 of the imaging device 4 show: an operation panel section 42 in a front side; two grip sections 43 in right and left sides; and illumination units 6 and an imaging section 7 in a lower side.

<<Medical Examination Apparatus>>

The medical examination apparatus 100 illustrated in FIG. 1 is medical equipment including: the imaging device 4 composed of a digital camera, an optical camera, a digital microscope, an optical microscope, or the like for use in surgeries and the like; an arm 3 movably supporting the imaging device 4; and a support column 2 supporting the arm 3.

The medical examination apparatus 100 only needs to be equipment which includes the imaging device 4 and is used for medical diagnoses and treatments in dentistry and the like, and the purpose of use, the installation place, the structures of the arm 3 and support column 2, and the like are not limited. Hereinafter, as an example of the medical examination apparatus 100, a dental treatment unit 1 on which the imaging device 4 is detachably mounted will be described with a root canal Sa (see FIG. 10B) being a subject S.

<<Dental Treatment Unit>>

The dental treatment unit 1 includes a treatment bed 10, the support column 2 stood on the treatment bed 10; the arm 3 axially supported on upper part of the support column 2; the imaging device 4 mounted on the distal end of the arm 3; and a display section 5 provided on the support column 2. The dental treatment unit 1 only needs to include the treatment bed 10, support column 2, arm 3, and imaging device 4, and the model, type, and the like thereof are not limited.

As illustrated in FIG. 1, the treatment bed 10 needs to include the support column 2 but is not limited to a treatment bed on which a patient lies.

The support column 2 is a column member rotatably supporting the proximal end of the arm 3. The support column 2 is composed of a metallic cylindrical member through which a harness 35 electrically connecting the imaging device 4 to a power supply and the like is inserted, for example. At the vertical center of the support column 2, the display section 5 is installed. On upper part of the support column 2, the proximal end of the arm 3 is swingably provided.

The arm 3 is composed of a balance arm arranged to extend from the support column 2 to the imaging device 4. The balance arm includes supporting power to elastically support the imaging device 4 so as to move the imaging device 4 up, down, left, right, forward, and backward by applying a force not less than a predetermined force (any force in a previously set direction of rotation) in the direction of movement. The arm 3 is composed of a multi-joint arm including a plurality of joints. The arm 3 includes a first arm 31 provided on the support column 2, a second arm 32 provided on the distal end of the first arm 31, and a third arm 33 which is provided on the distal end of the second arm 32 and supports the imaging device 4, for example. In the arm 3 (the first and second arms 31 and 32, for example), the harness 35 is inserted with the proximal end being in the support column 2 and the distal end being connected to a connector (not illustrated) provided for a housing 41 of the imaging device 4.

The first arm 31 is mounted to the support column 2 so as to rotate horizontally. The first arm 31 is elastically supported so as to rotate on a fitting 31a when receiving a horizontal force not less than a predetermined force. The proximal end of the first arm 31 is axially supported on the support column 2 with a first fixing member 31b so as not to swing horizontally.

The second arm 32 is provided with: a second rotary coupling member 32a which is elastically and swingably supported on a first arm 31 side of the second arm 32; a second vertical pivot member (not illustrated) which is elastically and swingably supported within a second rotation coupling member 32a side of the second arm 32; and a joint section 32b which is coupled to the distal end of the second arm 32 so as to be held at a proper angle.

As for the third arm 33, the proximal end is rotatably coupled to the joint section 32b of the second arm 32. In the coupling section at the distal end, an attachment member 34 to mount the imaging device 4 on the tip of the arm 3 is provided.

As illustrated in FIG. 1, the attachment member 34 is a coupling member to detachably couple the distal end of the third arm 33 to the imaging device 4. The attachment member 34 is composed of, for example, a detachable screw member to couple and fix a connecting section (not illustrated) located at the tip of the third arm 33 to a coupling section of the housing 41 of the imaging device 4.

Figure 2:
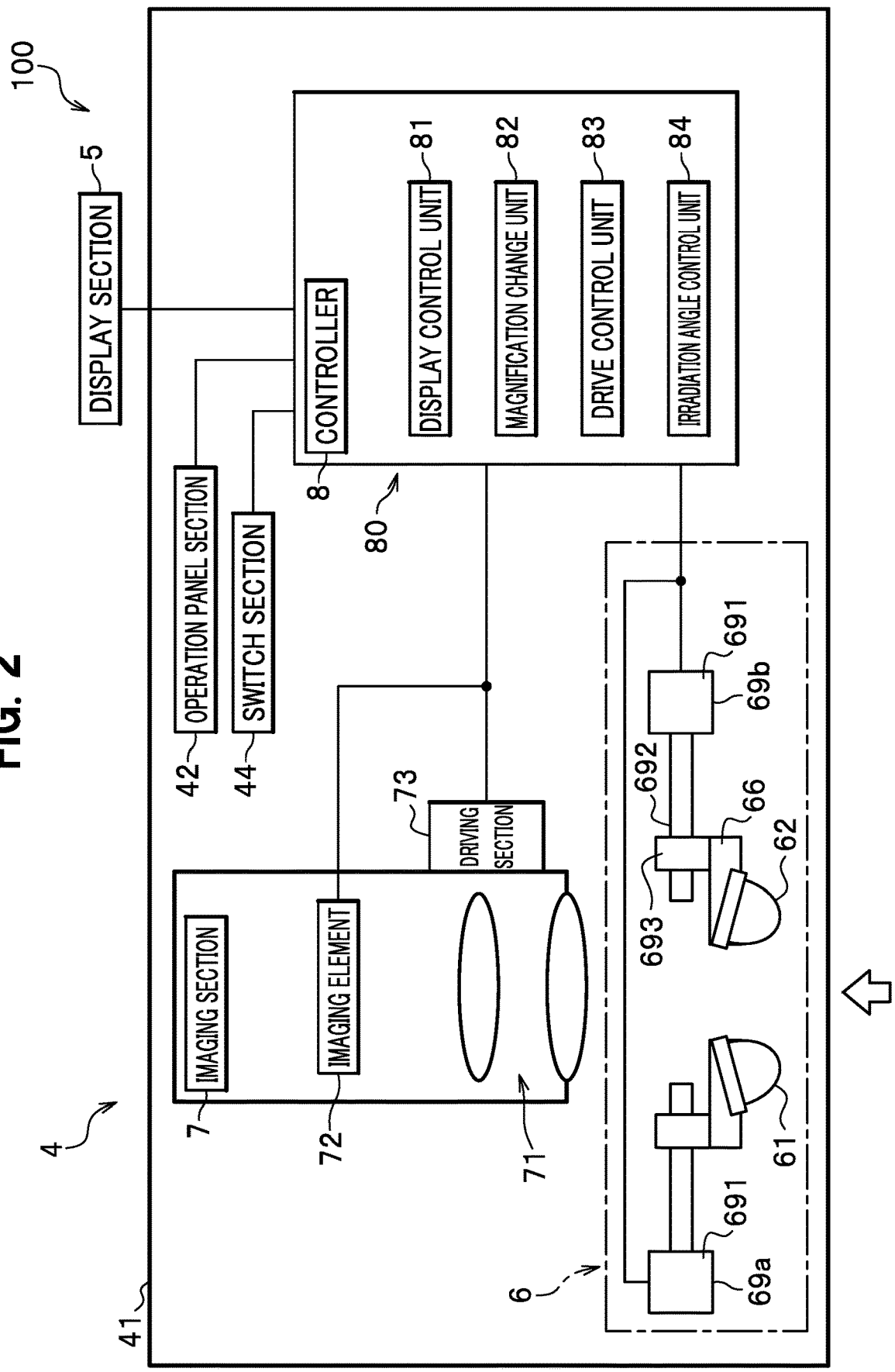
FIG. 2 is a block diagram of a medical optical imaging device according to the embodiment of the present invention.

As illustrated in FIGS. 1 and 2, the display section 5 is a display device to display medical information. The display section 5 is swingably installed on the support column 2. The display section 5 is electrically connected to the imaging device 4. The medical examination apparatus 100 is able to display medical information for use in the medical examination apparatus 100, video information of the imaging device 4, and the like by the display section 5.

<Imaging Device>

As illustrated in FIG. 1, the imaging device 4 is a digital camera, a surgical light camera, a digital microscope, or any imaging device for dental surgery which is detachably mounted on the tip of the arm 3, as described above. As illustrated in FIG. 2, the imaging device 4 includes the housing 41, the illumination units 6 emitting illumination light toward the subject S, the imaging section 7 imaging the subject S, and a controller 8 controlling the imaging section 7.

The illumination units 6 illustrated in FIGS. 4 to 7 may be provided to be fixed to the housing 41. The illumination units 6 may be operated manually using light-source driving sections 69a and 69b (see FIG. 9) or automatically operated with electricity. In the imaging device 4 of FIG. 2, accordingly, the illumination units 6 do not need the light-source driving sections 69a and 69b, and at least light-source mounted tables 66 may be provided to be fixed to the housing 41. Hereinafter, the imaging device 4 will be described.

<Housing>

As illustrated in FIGS. 3 to 7, the housing 41 is an imaging device body of the imaging device 4. The housing 41 is substantially box-shaped. The housing 41 includes: the operation panel section 42 provided on the front face; the grip sections 43 protruded on the right and left lateral faces; switch sections 44 provided for the right and left grip sections 43; a connected section (not illustrated) provided on the back face; and the illumination units 6 and imaging section 7 provided in the bottom face. The connected section (not illustrated) is composed of a substantially rectangular electric connection section which is integrated with the housing 41 and includes multiple connection terminals.

Figure 4:
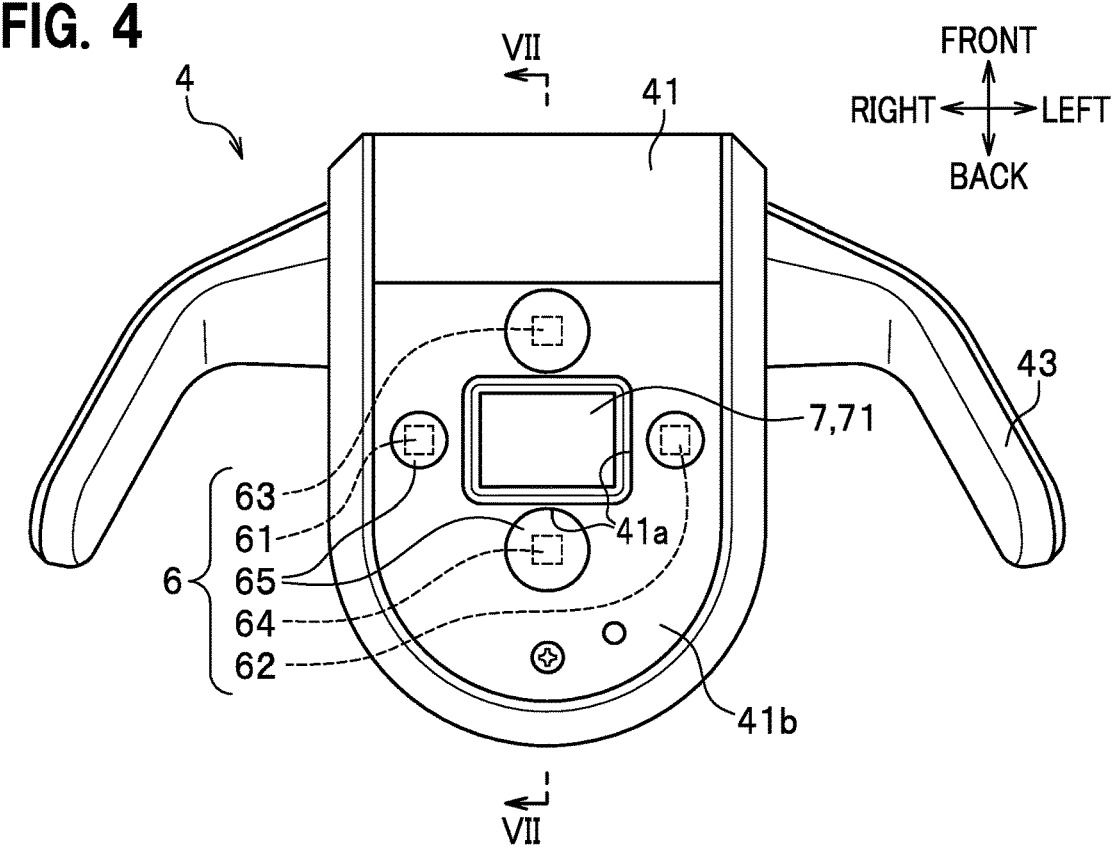
FIG. 4 is an enlarged bottom view of the medical optical imaging device.

As illustrated in FIG. 4, in the bottom face of the housing 41, a cover panel 41b is provided. The cover panel 41b includes installation holes 41a which allow illumination lenses 65 and an imaging lens system 71 to be arranged in an exposed manner. As illustrated in FIGS. 4 to 7, the illumination units 6 are provided to be fixed to the housing 41 in the example illustrated in these drawings.

Figure 5:
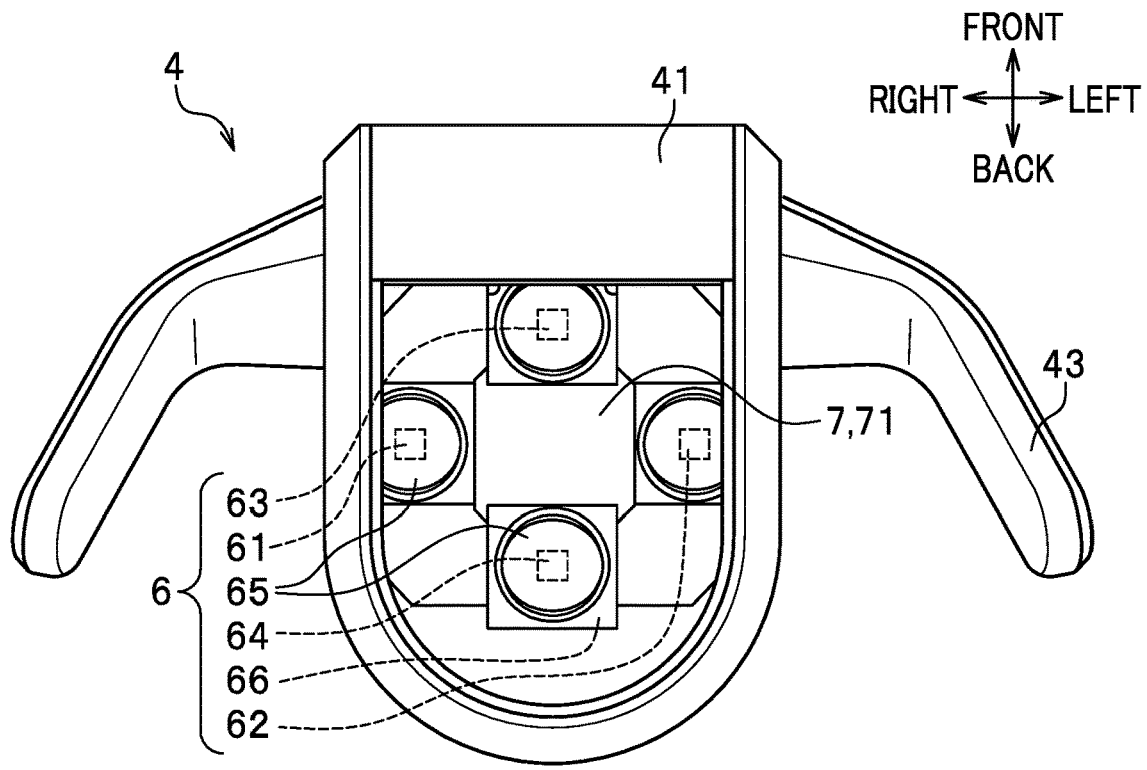
FIG. 5 is an enlarged bottom view illustrating the state of the medical optical imaging device with a cover removed.

In the bottom face of the housing 41, as illustrated in FIG. 5, the imaging lens system 71 of the imaging section 7 located at the center and the illumination lenses 65 (the illumination units 6) which are arranged on the front, back, left, and right sides of the periphery of the imaging lens system 71 and cover respective four light emitting elements 61 to 64 are assembled so as to appear when the cover panel 41b is removed.

Figure 6:
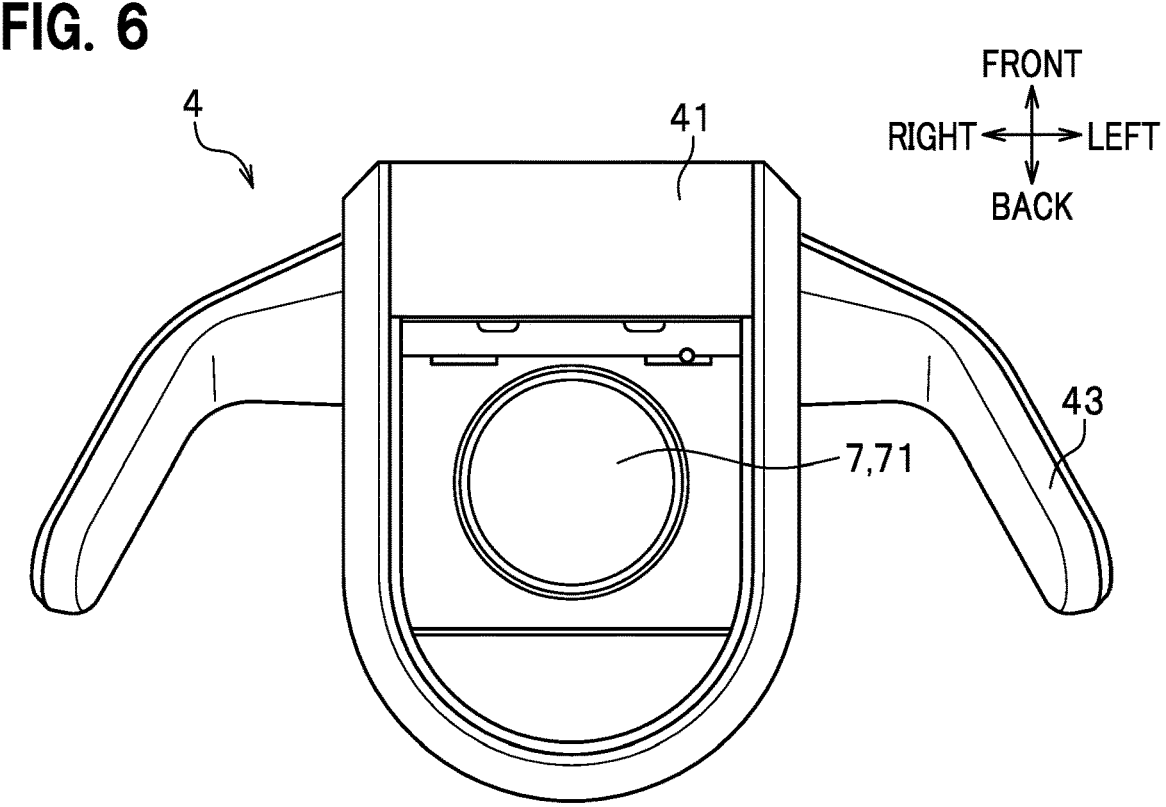
FIG. 6 is an enlarged bottom view illustrating the state of the medical optical imaging device with illumination units removed.
Figure 9:
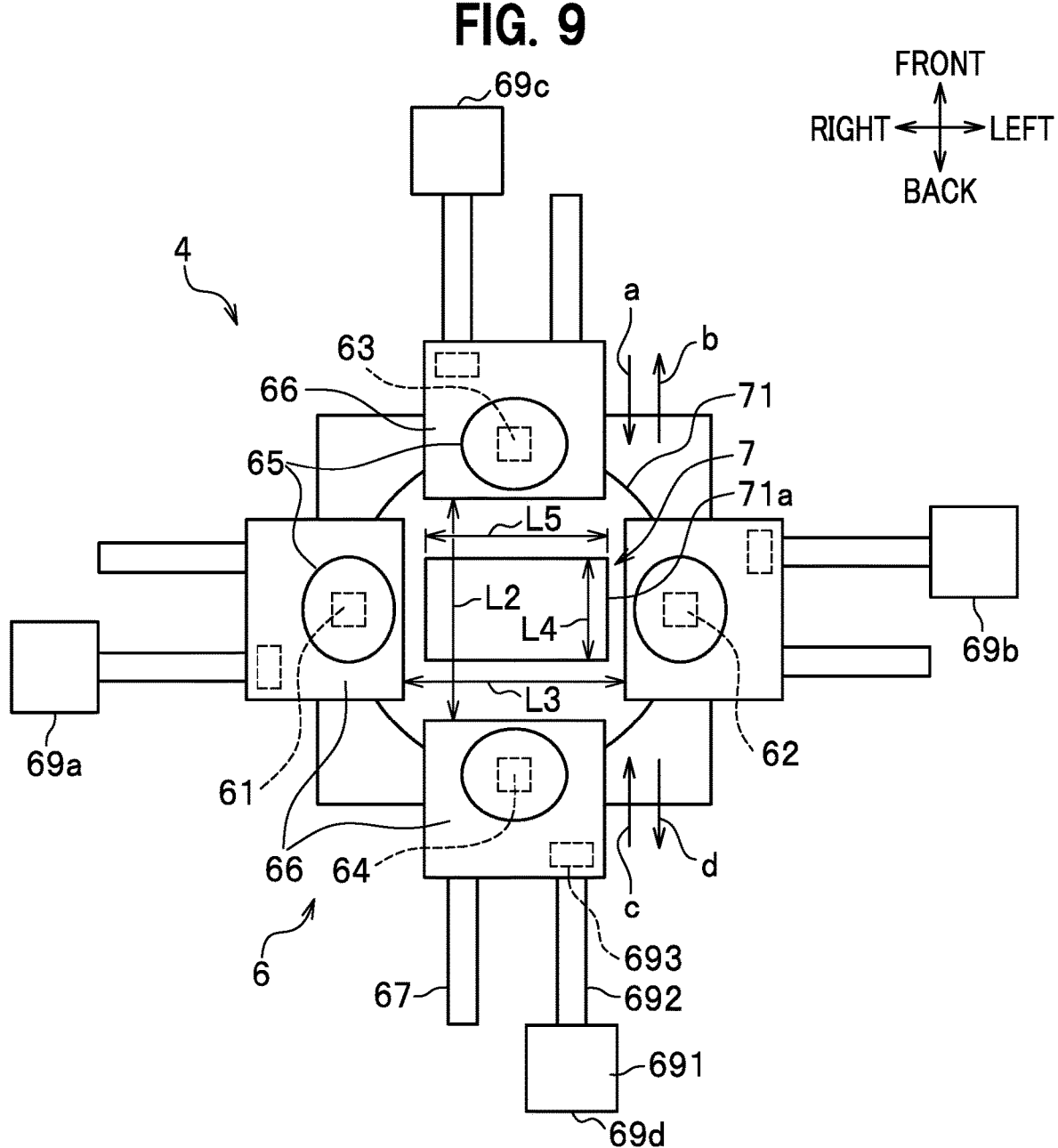
FIG. 9 is an explanatory view illustrating an arrangement of illumination units.

In the bottom face of the housing 41, when the illumination units 6 are removed, as illustrated in FIG. 6, the imaging lens system 71 appears larger than the imaging lens system 71 of FIG. 5 described above. In other words, the imaging lens system 71 is located so that the four light emitting elements 61 to 64 (the illumination units 6) located in front of the imaging lens system 71 overlap the imaging lens system 71 as viewed from the subject S side (see FIG. 9). As illustrated in FIGS. 9 and 10B, the illumination units 6 including the four light emitting elements 61 to 64 are arranged close to the center within a range where the illumination units 6 do not block an imaging light path R1 to an imaging element 72.

<Operation Panel Section>

Figure 3:
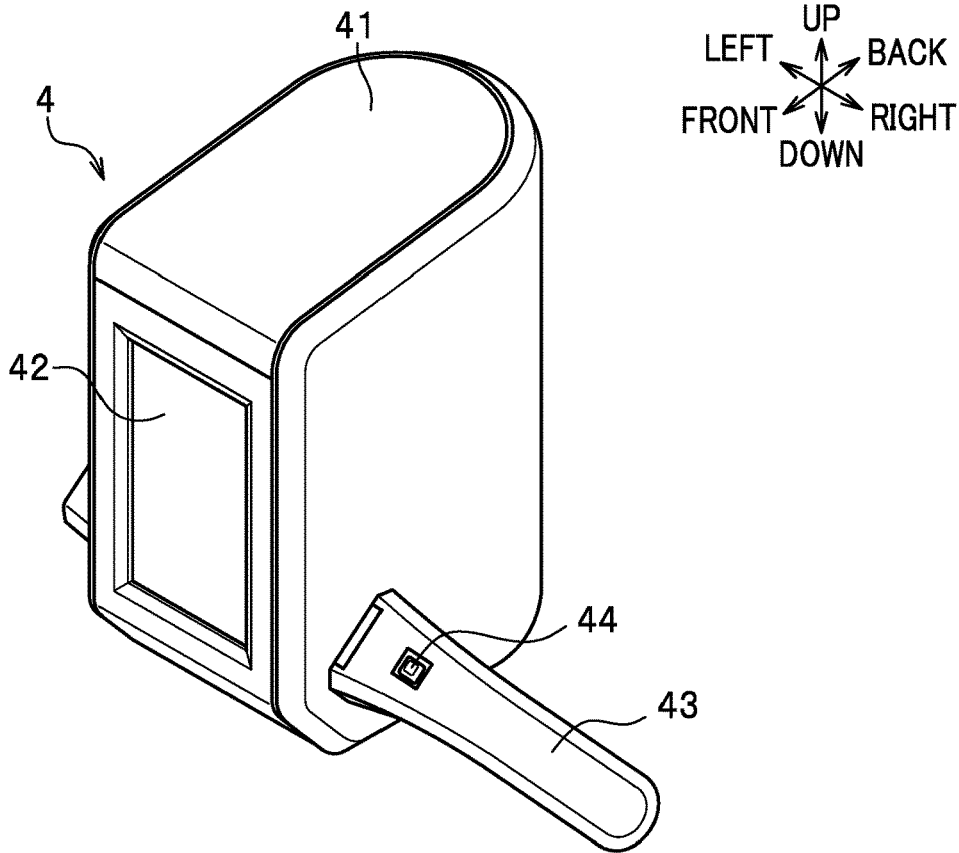
FIG. 3 is an enlarged perspective view of the medical optical imaging device.

The operation panel section 42 illustrated in FIG. 3 or 7 is a liquid crystal panel section including a plurality of touch switches (not illustrated) for operating the illumination units 6 or imaging section 7. The operation panel section 42 illustrated in FIG. 7 is electrically connected to the controller 8 of a circuit board 80 (see FIG. 2). Operation signals from the touch switches (not illustrated) are inputted to the controller 8 to drive the illumination units 6 and imaging section 7.

<Grip Section>

The grip sections 43 illustrated in FIGS. 3 and 4 are members which serve as a handle to operate the illumination units 6 or imaging section 7, to mount or demount the housing 41 onto or from the arm 3, or adjust the direction of the housing 41. Each grip section 43 is composed of a substantially bar-shaped members which is bent in a substantially L-shape (a shape with the both ends bent down) as viewed laterally. The grip sections 43 can be used as a handle for carrying the imaging device 4 separated from the arm 3.

<Switch Section>

As illustrated in FIG. 3, each switch section 44 is an autofocus switch for automatically adjusting the focus on the subject S (the root canal Sa or the like). The switch sections 44 may be a foot switch or a switch separately provided from the grip sections 43. As illustrated in FIG. 2, the switch sections 44 are electrically connected to the controller 8 of the circuit board 80 (see FIG. 7). Operation signals from the switch sections 44 are inputted to the controller 8 to drive the illumination units 6 and imaging section 7.

<Illumination Unit>

Figure 8A:
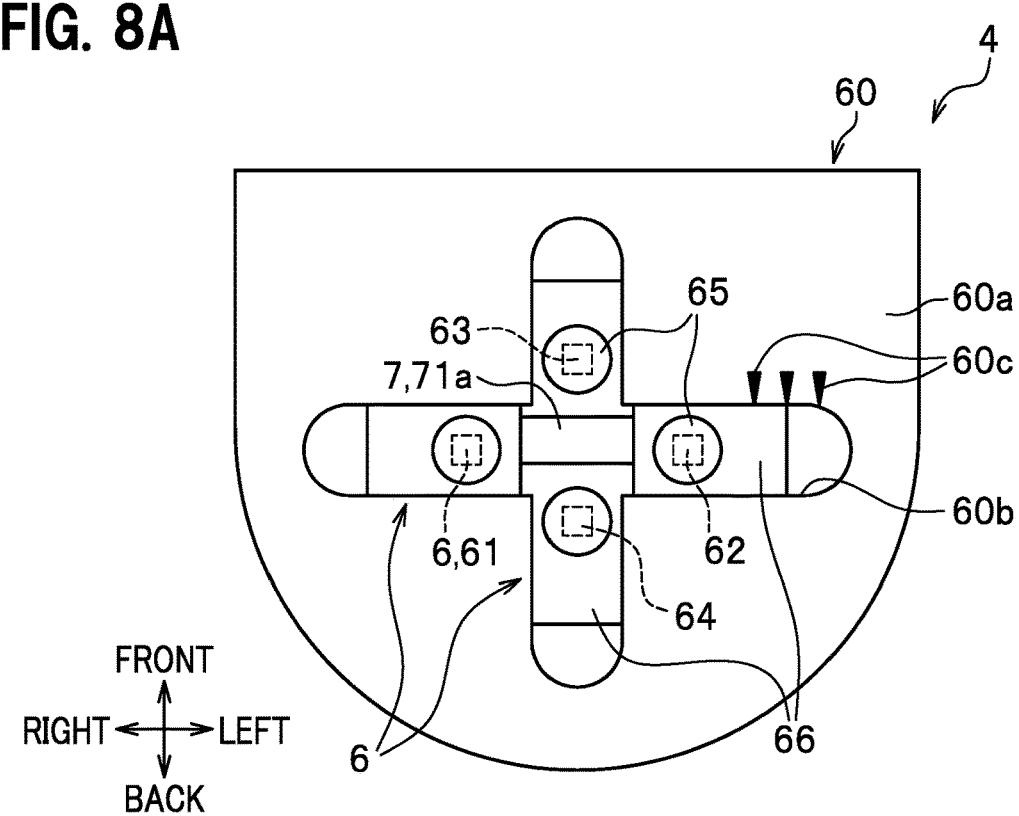
FIG. 8A is a schematic enlarged bottom view of the medical optical imaging device.
Figure 8B:
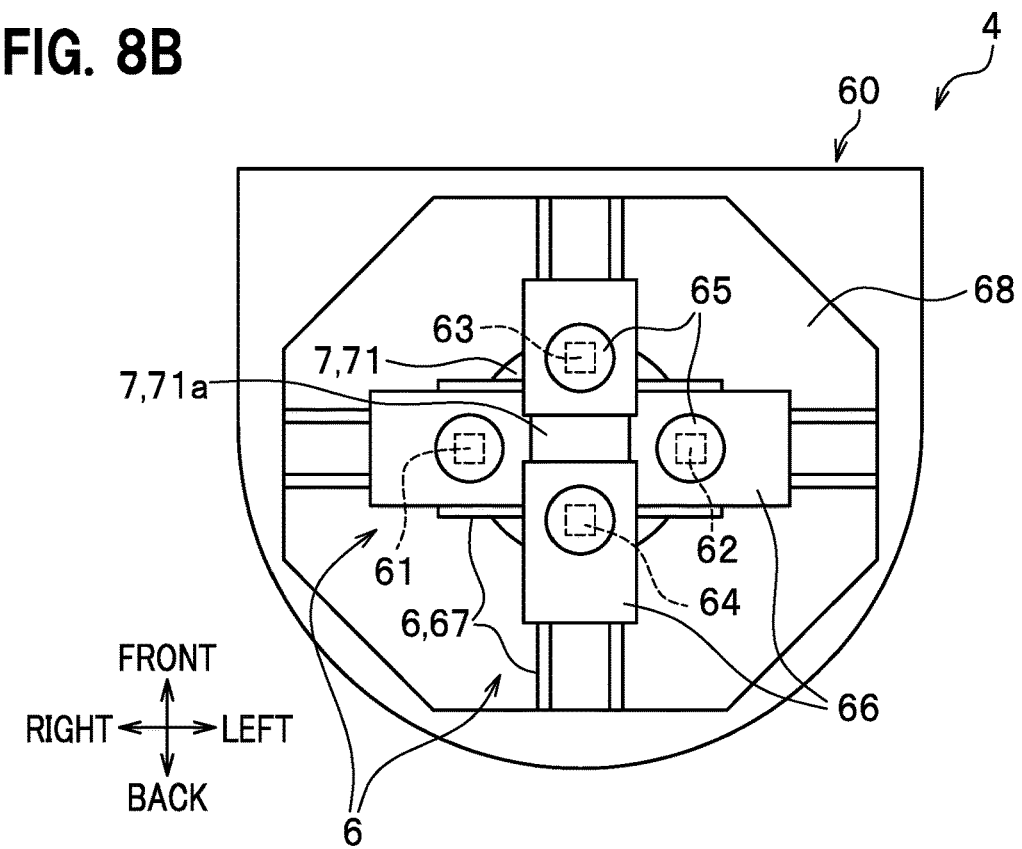
FIG. 8B is a schematic enlarged bottom view illustrating the state of the medical optical imaging device with the cover removed.

As illustrated in FIGS. 10B and 11B, the illumination units 6 are an illumination device to brightly illuminate the subject S, such as the inside of the patient's oral cavity, an objective tooth (tooth), or the inside of the root canal Sa. As illustrated in FIG. 8B, the illumination units 6 are provided with an illumination case body 60, the plurality of (for example, four) light emitting elements 61 to 64, the illumination lenses 65, the light-source mounted tables 66, rails 67, a rail mounted board member 68, and light-source driving sections 69a to 69d (see FIG. 9).

The light-source driving sections 69a to 69d (see FIG. 9) may be manually operated. The illumination units 6 do not need to include the light-source driving sections 69a to 69d (see FIG. 9) or do not need to include the rails 67, rail mounted board member 68, and light-source driving sections 69a to 69d (see FIG. 9) as illustrated in FIGS. 4 to 7. The illumination units 6 illustrated in FIGS. 4 to 7 therefore may be fixed to the housing 41 as described above. Hereinafter, an example of the illumination units 6 which includes the rails 67, rail mounted board member 68, and light-source driving sections 69a to 69d (see FIG. 9) will be described by way of example.

As illustrated in FIG. 8B, the illumination case body 60 is an illumination unit installation housing provided with the illumination units 6. As illustrated in FIG. 8A, in the lower side of the illumination case body 60, an illumination cover 60a including a window section 60b and a scale 60c is provided. The window section 60b is composed of a substantially x-shaped opening in which the light emitting elements 61 to 64 are arranged. The scale 60c is an indication scale that indicates the positions of the light emitting elements 61 to 64 in the forward, backward, leftward, and rightward (the optical axis Ax (see FIGS. 12A and 12B)) directions.

As illustrated in FIG. 10B, the illumination units 6 are configured such that when an imaging distance L1 from the imaging section 7 to the subject S is 300 to 500 mm, the illuminance around the subject S is not less than 7500 Lx. The illumination units 6 are located in front of the imaging lens system 71 so as to overlap the imaging lens system 71 as viewed from the subject S side and are located close to the center of the optical axes Ax of the imaging lens system 71. In addition, the illumination units 6 are located close to a range where the illumination units 6 do not block the imaging optical path R1 to the imaging element 72, preventing occurrence of mechanical vignetting, that is, partial darkening in an image due to the lens hood or the like. The illumination units 6 are thereby able to deliver light of the illumination units 6 deep into the root canal Sa to brightly illuminate the inside of the root canal Sa.

As illustrated in FIG. 9, the illumination units 6 are arranged such that the aspect ratio (the ratio of vertical length L4 of the light reception surface to horizontal length L5 of the light reception surface) of the light-reception surface (a sensor light-reception area 71a) of the imaging lens system 71 is substantially equal to the aspect ratio of the display size of the display section 5 (see FIG. 1) that displays an image captured by the imaging section 7.

As illustrated in FIGS. 8B and 9, the light emitting elements 61 to 64 are composed of four LEDs irradiating the subject S. The light emitting elements 61 to 64 are mounted on the respective light-source mounted tables 66 located on the front, back, left, and right sides in the bottom view. At least one of the plurality of light emitting elements 61 to 64 is composed of an illuminant having a peak wavelength of 380 to 500 nm. For example, the light emitting elements 61 and 62 positioned on the left and right sides are composed of blue light emitting diodes having a peak wavelength of 405 nm. The light emitting elements 63 and 64 positioned on the front and back sides are composed of white light emitting diodes with 25,000 Lx. As illustrated in FIGS. 10B and 11B, the optical axes 6a of the light emitting elements 61 to 64 are arranged so as to pass through an opening Sb of the root canal Sa and intersect at an acute angle $\theta 1$, allowing for bright illumination within the root canal Sa. The acute angle $\theta 1$ is 4 to 11 degrees in the front-back direction and is 5 to 13 degrees in the left-right direction, for example. Preferably, the acute angle $\theta 1$ is 5.6 to 9.6 degrees in the front-back direction and is 6.6 to 11.6 degrees in the left-right direction.

At least two of the plurality of light emitting elements 61 to 64 (the illumination units 6) are arranged so that illumination light beams therefrom intersect on the irradiation area. The light emitting elements 61 to 64 may include the illumination lenses 65 (integrated type) as illustrated in FIGS. 10B, 11B, 12A, and 12B or may be separated from the illumination lenses 65.

The type, structure, shape, and the like of the light emitting elements 61 to 64 are not limited. The light emitting elements 61 to 64 may also be chip-type LEDs, lens-integrated LEDs, or different type LEDs.

As illustrated in FIGS. 8A, 8B, and 9, the illumination lenses 65 are transparent lens members that cover the respective four light emitting elements 61 to 64. The illumination lenses 65 are located under the light emitting elements 61 to 64 and are fixed to the light-source mounted tables 66. The four illumination lenses 65 are arranged so that light beams emitted from the four light emitting elements 61 to 64 intersect at a single point.

As illustrated in FIG. 9, the light-source mounted tables 66 are plates with the respective four light emitting elements 61 to 64 mounted thereon. The light-source mounted tables 66 are mounted on the rails 67 so as to freely reciprocate and are located so as to move toward and away from the sensor light-reception area 71a by the light-source driving sections 69a to 69d.

As illustrated in FIG. 8B, the rails 67 are guide members that guide movement of the light-source mounted tables 66. When viewed from the bottom, the rails 67 are extended from around the center (the sensor light-reception area 71a) forward, backward, leftward, or rightward. The rails 67 are arranged in parallel to the rail mounted board member 68.

The rail mounted board member 68 illustrated in FIG. 8B is a board member on which the rails 67 are placed. The rail mounted board member 68 is horizontally mounted on the illumination case body 60.

As illustrated in FIG. 9, the light-source driving sections 69a to 69d are driving devices to individually move the light emitting elements 61 to 64 toward and away from the center of the four light emitting elements 61 to 64 (forward, backward, leftward, or rightward) to change the arrangement positions thereof. The light-source driving sections 69a to 69d may be electric driving devices driven by a driving source such as an electric motor or a linear motor or may be manual devices manually operated. Hereinbelow, electric driving devices will be described as an example of the light-source driving sections 69a to 69d.

Each of the light-source driving sections 69a to 69d includes an electric motor 691, a male thread member 692, and a female thread member 693. The light-source driving sections 69a to 69d are located at four places on the front, back, left, and right sides, for example. The light-source driving sections 69a to 69d may be provided at two places on the front and back sides, instead of four places.

The electric motors 691 are driving sources to reciprocate the light emitting elements 61 to 64 placed on the respective light-source mounted tables 66.

The male thread members 692 are members rotated and driven by the respective electric motors 691. The male thread members 692 are extended along the corresponding rails 67 in parallel thereto.

The female thread members 693 are members which are screwed with the respective male thread members 692 and reciprocate along the corresponding rails 67. The female thread members 693 are fixed to the respective light-source mounted tables 66 with the light emitting elements 61 to 64 mounted thereon to drive and reciprocate the light-source mounted tables 66.

<Imaging Section>

As illustrated in FIG. 2, the imaging section 7 is an imaging device section that images the subject S within the patient's oral cavity. The imaging section 7 includes: the imaging lens system 71; the imaging element 72 receiving an optical image formed by the imaging lens system 71; and a driving section 73 to change the arrangement of the illumination units 6. As illustrated in FIG. 10B, the imaging section 7 includes an autofocus function. An intersection 6b in which the optical axes 6a of the light emitting elements 61 to 64 intersect at the acute angle ($\theta 1$) is located in a focal range of the imaging lens system 71 by the autofocus function.

The focus of the imaging section 7 is fixed focus. In this case, the fixed focus is located near the intersection 6b in which the optical axes 6a of the light emitting elements 61 to 64 intersect at the acute angle $\theta 1$.

The imaging lens system 71 is composed of a plurality of lenses and is located above the illumination units 6 (on the imaging element 72 side).

The imaging element 72 is composed of an image receiving sensor, such as a CMOS or a CCD.

Figure 12A:
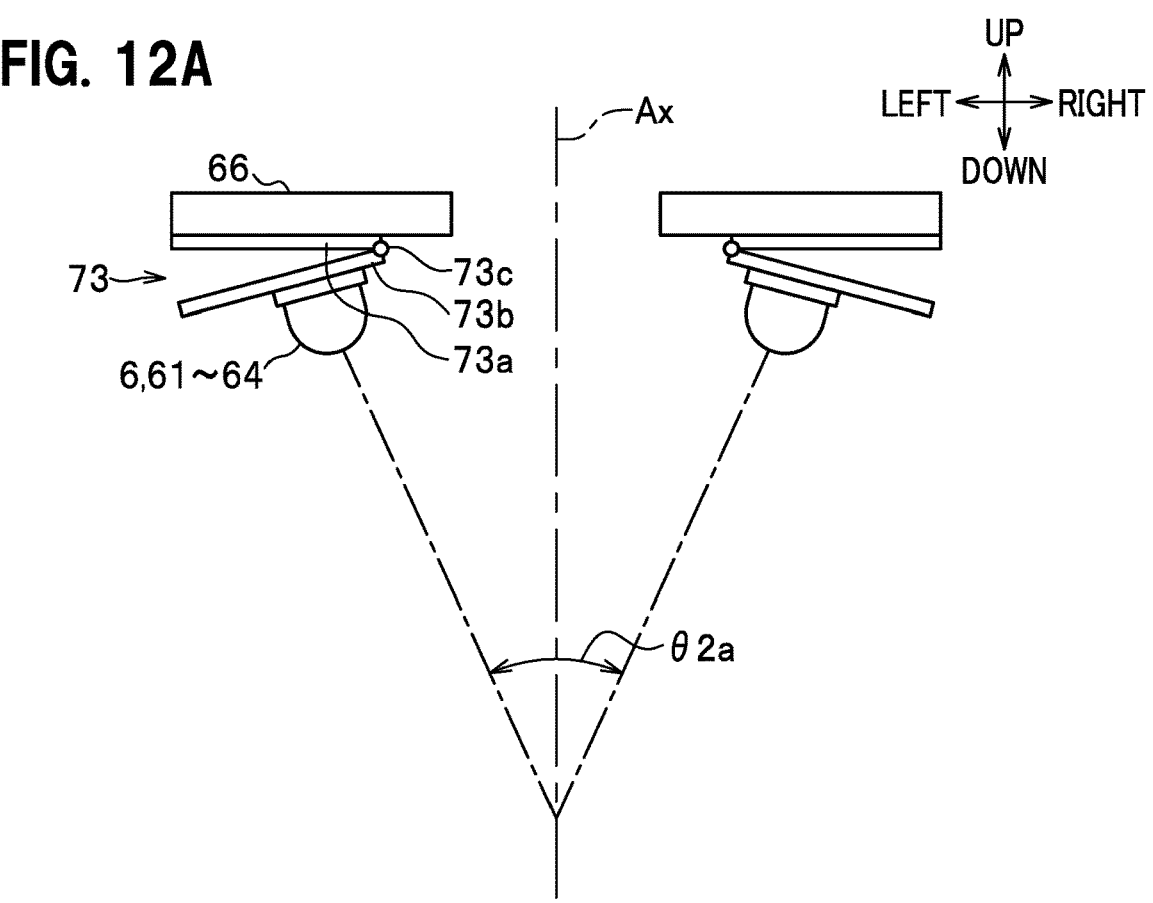
FIG. 12A is an explanatory view illustrating the state of the illumination units for a small magnification.
Figure 12B:
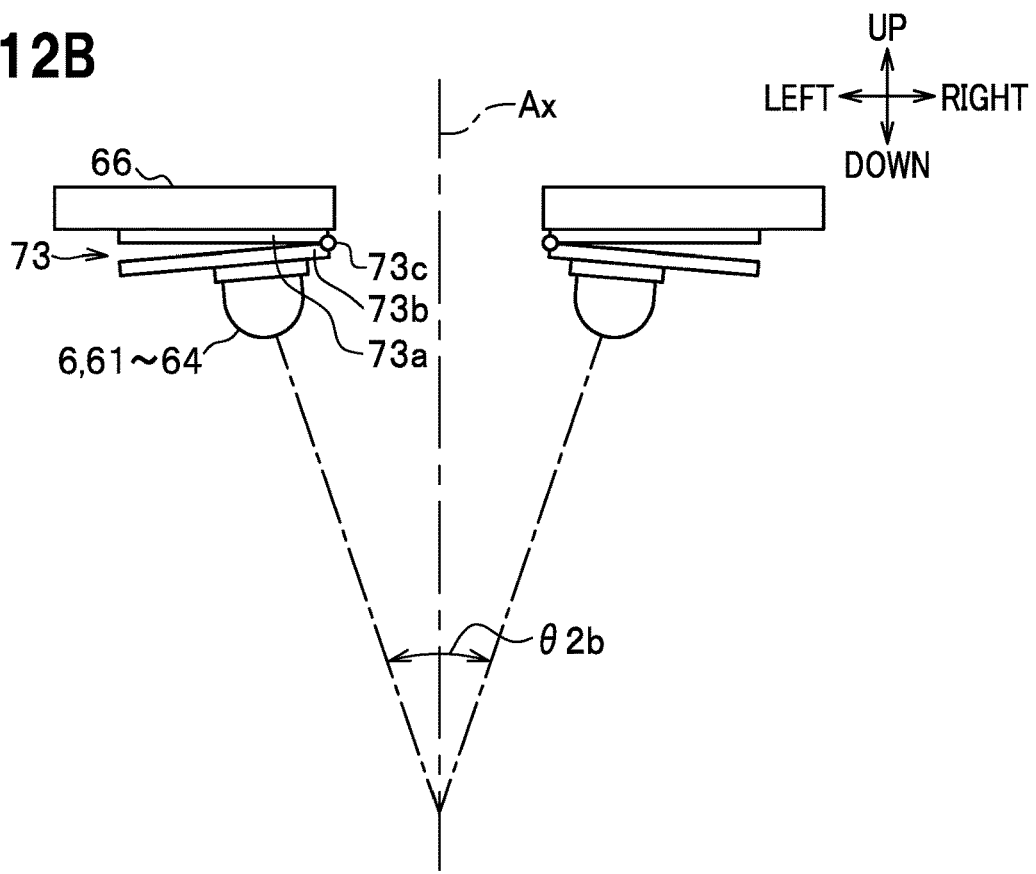
FIG. 12B is an explanatory view illustrating the state of the illumination units for a large magnification.

As illustrated in FIG. 12A, the driving sections 73 are irradiation angle adjustment devices which drive the light emitting elements 61 to 64 so as to increase an irradiation angle $\theta 2a$ when the imaging section 7 reduces the magnification for an image to be captured. As illustrated in FIG. 12B, the driving section 73 drives the light emitting elements 61 to 64 so as to reduce an irradiation angle $\theta 2b$ when the imaging section 7 increases the magnification for an image to be captured.

As illustrated in FIGS. 12A and 12B, each driving section 73 includes a fixed section 73a, an illumination unit tilting section 73b, and an electric motor 73c.

The fixed section 73a is a plate member fixed to the light-source mounted table 66. At an end of the fixed section 73a closer to the optical axis Ax of the imaging section 7, the electric motor 73c is provided.

The illumination unit tilting section 73b is a plate member which is tilted about the driving shaft of the electric motor 73c by the electric motor 73c to change the irradiation angle θ2a, θ2b. The proximal end (the end closer to the optical axis Ax of the imaging section 7) of the illumination unit tilting section 73b is swingably coupled to the driving shaft of the electric motor 73c. On the lower surfaces of the illumination unit tilting sections 73b, the light emitting elements 61 to 64 are mounted.

The electric motor 73c is a driving source to tilt the illumination unit tilting section 73b about the proximal end swingably coupling the illumination unit tilting section 73b and fixed section 73a. As illustrated in FIG. 2, the electric motor 73c is electrically connected to an irradiation angle control unit 84 and is driven by operation for the operation panel section 42 or switch sections 44.

<Controller>

As illustrated in FIG. 2, the controller 8 includes a display control unit 81, a magnification change unit 82, a drive control unit 83, and the irradiation angle control unit 84. The electric circuit constituting the controller 8 is provided in the circuit board 80 placed in the housing 41 illustrated in FIG. 7.

<Display Control Unit>

The display control unit 81 illustrated in FIG. 2 is a control device performing control to display a captured image on the display section 5. The display control unit 81 performs at least one of moving the imaging lens system 71 and executing image processing for imaging data acquired from the imaging element 72 such that the illumination units 6 are not displayed when the illumination units 6 block the imaging optical path R1 to the imaging element 72, and displays the captured image on the display section 5.

<Magnification Change Unit>

The magnification change unit 82 is a magnification change device that changes the magnification for an image to be captured by the imaging section 7. The magnification change unit 82 changes the magnification by at least one of moving the imaging lens system 71 and executing image processing, including magnifying, for the imaging data acquired from the imaging element 72. The driving sections 73 are configured to operate based on the magnification.

<Drive Control Unit>

The drive control unit 83 illustrated in FIG. 2 is a drive control device that automatically controls the driving sections 73 to change the arrangement positions of the light emitting elements 61 to 64 of the illumination units 6. The drive control unit 83 is electrically connected individually to the light-source driving sections 69a, 69b, 69c, and 69d.

The irradiation angle control unit 84 is an irradiation angle control device to control the angle of the irradiation angle θ2 of the illumination units 6 illustrated in FIGS. 10B and 11B. The irradiation angle control unit 84 controls the irradiation angle θ2 based on the magnification which was changed by the magnification change unit 82 for an image to be captured by the imaging section 7, thus emitting illumination light toward the root canal Sa and providing good visibility deep in the root canal Sa (see FIG. 2) <<Operation>>

Next, the operation of the medical examination apparatus 100 according to the embodiment will be described with reference to FIGS. 1 to 15, mainly FIGS. 14 and 15.

The imaging device 4 illustrated in FIG. 1 is mounted on the tip of the arm 3 for use at dental examinations. For a dental examination, first, the first to third arms 31, 32, and 33 are swung to align the direction of the imaging device 4 with the direction of the position of the root canal Sa as the subject S.

Next, with reference to mainly FIG. 14, the following description is given of the case of automatically changing the arrangement of the illumination units 6 without manual zooming.

First, the operation panel section 42 or switch sections 44 illustrated in FIG. 2 are operated to set the magnification change unit 82 to a desired magnification. When the operation of setting the magnification is performed (Yes in Step S1), the controller 8 acquires positional information of the illumination units 6 for the set magnification (Step S2). When the operation of setting the magnification is not performed (No in Step S1), the controller 8 continues to monitor whether the setting operation is performed.

When the positional information of the illumination units 6 for the magnification is acquired in Step S2, the irradiation angle control unit 84 drives the light-source driving sections 69a to 69d (the electric motors 691) and moves the light emitting elements 61 to 64 forward, backward, leftward, or rightward to adjust intervals W1 between the light emitting elements 61 to 64 (the illumination units 6) for arrangement change of the light emitting elements 61 to 64. As for the light emitting elements 61 to 64, as illustrated in FIG. 9, distance L2 between two opposite light emitting elements 61 and 62 or light emitting elements 63 and 64 (the intervals W1 between the opposite ones of the light emitting elements 61 to 64) is thus adjusted, and the irradiation angle θ2 of the illumination units 6 is changed depending on the distance L2.

Figure 15:
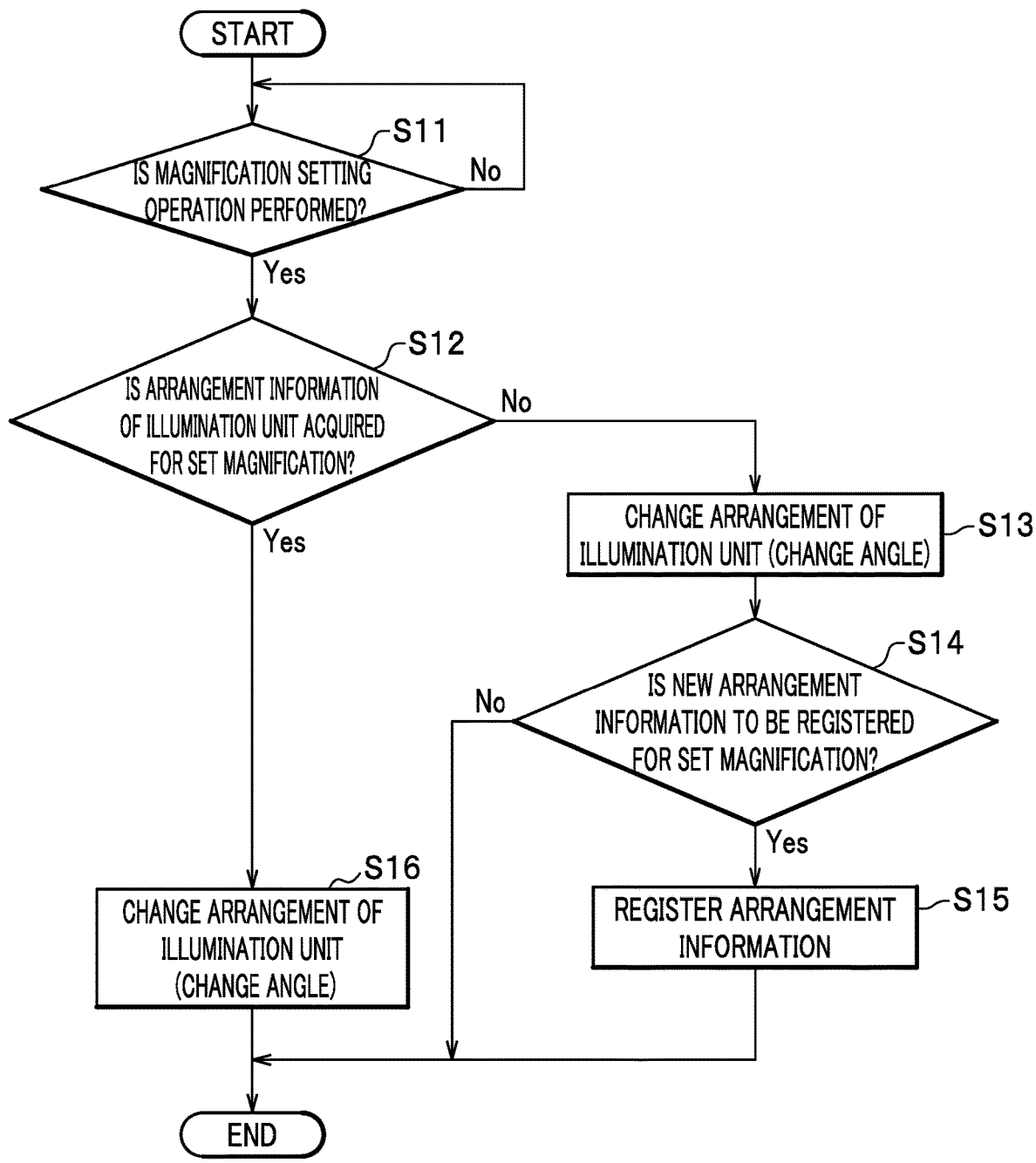
FIG. 15 is a flowchart illustrating control to automatically change the arrangement of the illumination units for manual zooming.

Next, with reference to mainly FIG. 15, the following description is given of the case of automatically changing the arrangement of the illumination units 6 for manual zooming.

First, the operation panel section 42 or switch sections 44 illustrated in FIG. 2 are operated to set the magnification change unit 82 to a desired magnification. When the operation of setting the magnification is performed (Yes in Step S11), the process proceeds to Step S12. When the operation of setting the magnification is not performed (No in Step S11), the controller 8 continues to monitor whether the setting operation is performed.

The controller 8 acquires arrangement information of the illumination units 6 for the set magnification. When the arrangement information of the illumination units 6 for the magnification is acquired in Step S12 (Yes in Step S12), the irradiation angle control unit 84 drives the light-source driving sections 69a to 69d (the electric motors 691) and moves the light emitting elements 61 to 64 forward, backward, leftward, or rightward to adjust the intervals W1 between the light emitting elements 61 to 64 (the illumination units 6) for arrangement change of the light emitting elements 61 to 64 (Step S16). For the light emitting elements 61 to 64, as illustrated in FIG. 9, the distance L2 between two opposite light emitting elements 61 and 62 or light emitting elements 63 and 64 (the intervals W1 between the opposite ones of the light emitting elements 61 to 64) is thus adjusted, and the irradiation angle θ2 of the illumination units 6 is changed depending on the distance L2 (Step S16). The process is terminated when the irradiation angle θ2 is changed.

When no arrangement information of the illumination units 6 is acquired in Step S12 (No in Step S12), similarly to Step S16, the irradiation angle control unit 84 changes the arrangement of the illumination units 6 and changes the angle θ1 of the optical axes 6a and the irradiation angle θ2 (Step S13). The process proceeds to Step S14.

Next, the arrangement information of the illumination units 6 for the set magnification is newly registered (Step S14). If the registration is to be performed (Yes in Step S14), the arrangement information is registered (Step S15), and the process is terminated. If the registration is not to be performed (No in Step S14), the process is terminated without registration of the arrangement information.

The illumination units 6 are thus controlled by the controller 8.

As illustrated in FIG. 2 or 10B, the present invention is the medical optical imaging device 4 including: the illumination units 6 emitting illumination light toward the subject S; the imaging section 7 imaging the subject S; and the controller 8 controlling at least the imaging section 7. The imaging section 7 includes the imaging lens system 71 and the imaging element 72 receiving an optical image formed by the imaging lens system 71, and the illumination units 6 are located in front of the imaging lens system 71 to overlap the imaging lens system 71 as viewed from the subject S side.

In the medical optical imaging device 4, since the illumination units 6 are located in front of the imaging lens system 71 to overlap the imaging lens system 71 as viewed from the subject S side, the illumination units 6 can be located close to the center of the optical axes Ax of the imaging lens system 71. The illumination units 6 are thereby able to deliver light deep into the root canal Sa that is composed of a thin and deep hole to brightly illuminate the inside of the root canal Sa. This improves the efficiency of medical examinations and facilitates treatments.

Furthermore, the illumination units 6 may be arranged in the aspect ratio of the light reception surface (the sensor light-reception area 71a) of the imaging lens system 71 so as to avoid the optical path to the imaging element 72 of the imaging section 7, for example. This implements an illumination structure near coaxial illumination with the surrounding illumination. The illumination units 6 need a smaller number of expensive components, such as a mirror, leading to cost reduction of the medical optical imaging device 4.

The present invention thus provides a small-sized and unexpensive medical optical imaging device capable of illuminating deep in a root canal.

As illustrated in FIG. 9, 10B, or 11B, the illumination units 6 are composed of the plurality of light emitting elements 61 to 64 irradiating the subject S. The subject S is the root canal Sa, and the optical axes 6a of the light emitting elements 61 to 64 are arranged so as to intersect at the acute angle θ1 after passing through the opening Sb of the root canal Sa.

Thus, the illumination units 6 of the present invention illustrated in FIG. 11B are configured so that the optical axes 6a of the light emitting elements 61 to 64 intersect within the root canal Sa at an angle θ1 which is more acute than an angle θ10 between optical axes 600a of a comparative example (see FIG. 11A). The intervals W1 between the light emitting elements 61 to 64 is shorter than an interval W10 between light emitting elements 610 and 620 (see FIG. 11A) of the comparative example. In the illumination units 6 of the present invention, distance L6 from the opening Sb of the root canal Sa to the intersection 6b of the optical axes 6a can be made longer than distance L60 from the opening Sb of the root canal Sa to the intersection 6b of the optical axes 600a of the comparative example, allowing for imaging of the inside of the root canal Sa, or deep part of the inner wall of the root canal Sa. The illumination units 6 of the present invention thus brightly illuminate the inside of the root canal Sa, improving the visibility of the root canal Sa.

As illustrated in FIG. 10B, the imaging section 7 includes an autofocus function, and the intersection 6b in which the optical axes 6a intersect at the acute angle θ1 is located within the focal range of the imaging lens system 71 by the autofocus function.

Locating the intersection 6b within the depth of field allows the imaging section 7 to provide a clear image of the root cabal Sa at the focal position.

As illustrated in FIG. 3, the imaging device 4 further includes the grip sections 43 to operate the illumination units 6 and/or imaging section 7 (see FIG. 4), and the grip sections 43 include the switch sections 44 to execute the autofocus function.

Since the grip sections 43 to operate the illumination units 6 and/or imaging section 7 (see FIG. 4) include the switch sections 44 to execute the autofocus function, the imaging device 4 can be moved toward an imaging object while the switch sections 44 are operated, thus enhancing the convenience for the user. Furthermore, the illumination units 6 and/or the imaging section 7 (see FIG. 4) can be intuitively operated.

As illustrated in FIGS. 11A and 11B, the focus of the imaging section 7 is fixed focus, and the fixed focus is located near the intersection 6b in which the optical axes 6a intersect at the acute angle θ1.

The imaging section 7 also provides a clear image of the root cabal Sa for the fixed focus.

Furthermore, one of the plurality of light emitting elements 61 to 64 illustrated in FIG. 9 emits light with a peak wavelength of 380 to 500 nm.

The light emitting elements 61 to 64 of the illumination units 6 include not only white LEDs but also blue LEDs, thus enabling formation of fluorescence images of plaque, resin, and the like. Employing LEDs as the light sources of the illumination units 6 can lead to miniaturization of the whole imaging device 4 and provide high intensity of light with low-power light sources.

Figure 13A:
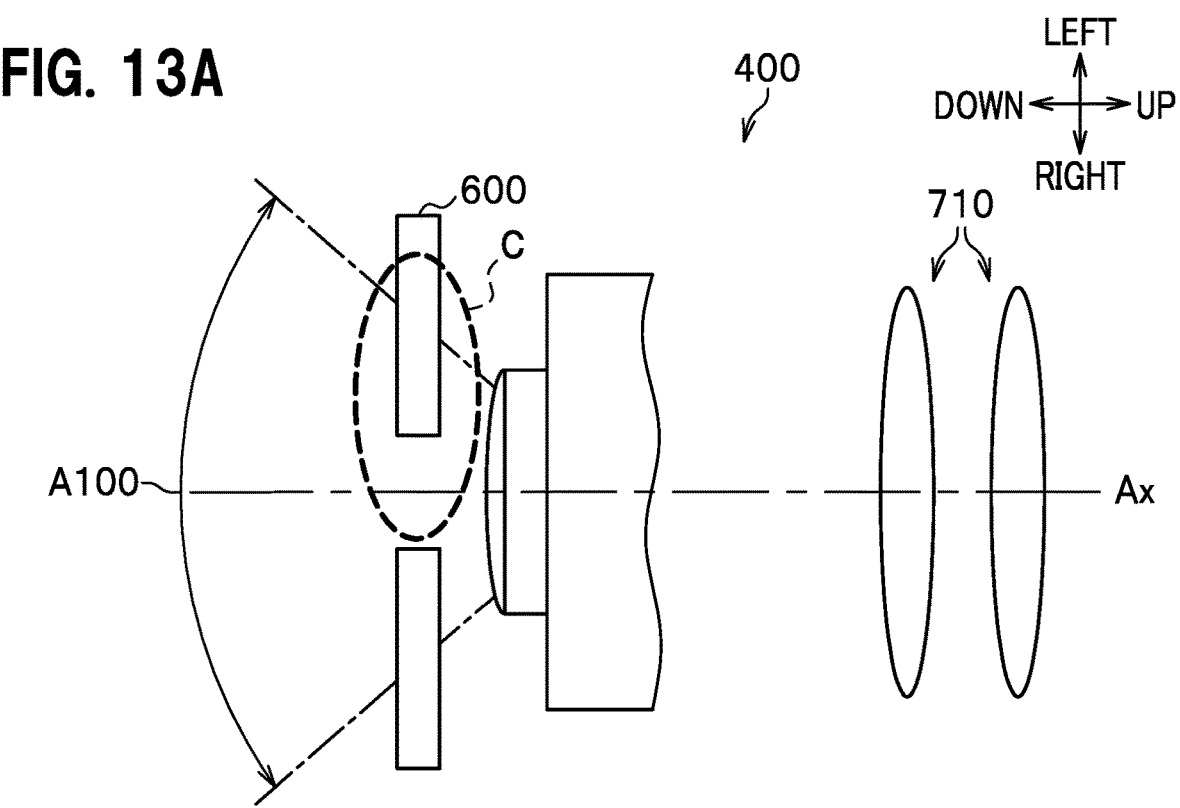
FIG. 13A is an explanatory view illustrating the illumination unit of the comparative example that produces mechanical vignetting.
Figure 13B:
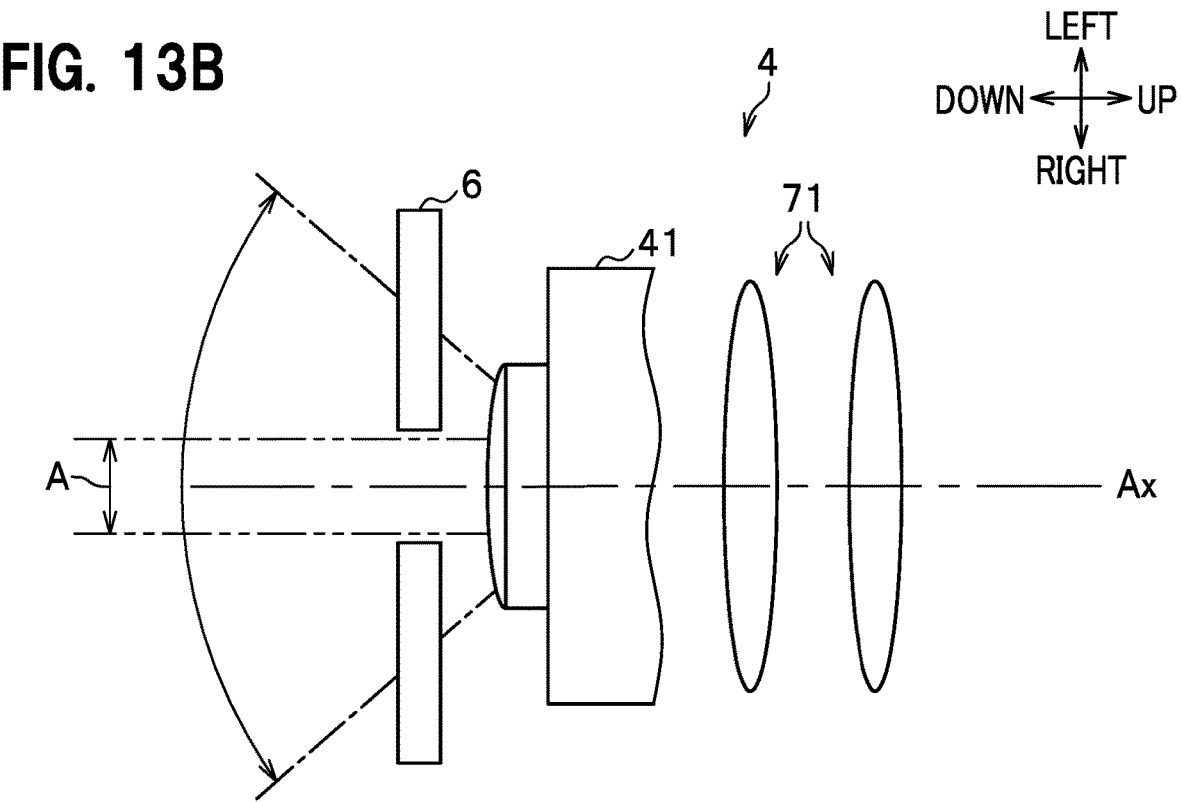
FIG. 13B is an explanatory view illustrating the illumination units of the present invention that produce no mechanical vignetting.

As illustrated in FIGS. 10B and 13B, the illumination units 6 are located close to a range where the illumination units 6 do not block the imaging optical path R1 to the imaging element 72.

Since the illumination units 6 are not located within the imaging optical path R1, it is possible to prevent occurrence of mechanical vignetting, that is, partial darkening in an image due to the lens hood or the like.

As illustrated in FIG. 2, the controller 8 includes the display control unit 81 to display a captured image on the display section 5. The display control unit 81 performs at least one of moving the imaging lens system 71 and executing image processing for imaging data acquired from the imaging element 72 such that the illumination units 6 are not displayed when the illumination units 6 block the imaging optical path R1 to the imaging element 72 (see FIG. 10B), and displays the captured image on the display section 5.

By locating the illumination units 6 within the imaging optical path R1, the controller 8 can set the illumination units 6 closer to the center of the optical axes 6a. Image processing can be executed to display image part not including mechanical vignetting on the display section 5, thus providing the best surgical field information to a surgeon using the medical examination apparatus 100.

As illustrated in FIG. 13A, for the positional relationship between the angle of view at wide-angle imaging with an angle range A100 being wide and an illumination unit 600, the illumination unit 600 is located within the imaging optical path R1 (see FIG. 10B) with the magnification being low, producing mechanical vignetting. In contrast, according to the present invention, the illumination units 6 are located close to a range where the illumination units 6 do not block the imaging optical path R1 of the imaging element 72 by changing the position of the imaging lens system 71 to the telephoto imaging (high-magnification) position with a wide-angle range A being small. This prevents the illumination units 6 from producing mechanical vignetting.

For example, the positional information of the imaging lens system 71 (mainly a zoom lens) is acquired, and the imaging lens is thereby prevented from being positioned such that the imaging lens can produce mechanical vignetting. This prevents occurrence of mechanical vignetting. Even if the illumination units 6 are located within the angle of view, for example, image processing is executed so as to display image part not including mechanical vignetting, thus displaying an image free of mechanical vignetting.

As illustrated in FIG. 10B, the illumination units 6 are configured such that when the imaging distance L1 from the imaging section 7 to the subject S is 300 to 500 mm, the illuminance around the subject S is not less than 7500 Lx.

The illumination units 6 are thus configured to provide at least a certain light intensity within the imaging distance L1. The illumination units 6 therefore are able to irradiate the root canal Sa brightly with light up to the depth (10 mm, for example) required by the surgeon.

As illustrated in FIG. 9, the illumination units 6 are arranged such that the aspect ratio of the light-reception surface (the sensor light-reception area 71a) of the imaging lens system 71 is substantially equal to the aspect ratio of the display size on the display section 5, of an image captured by the imaging section 7.

The screen aspect ratio of the display section 5 therefore is set substantially equal to the aspect ratio of the light-reception surface (the sensor light-reception area 71a) of the imaging lens system 71, thus reducing unnecessary image processing.

As illustrated in FIG. 2, the controller 8 includes the magnification change unit 82 which changes the magnification for an image to be captured by the imaging section 7. The imaging section 7 includes the driving sections 73 to change the arrangement of the illumination units 6. The magnification change unit 82 changes the magnification by at least one of moving the imaging lens system 71 and executing image processing for the imaging data acquired from the imaging element 72. The driving sections 73 are operated based on the magnification.

When the magnification for an image to be captured by the imaging section 7 is changed, the light-reception area is reduced, and the illumination units 6 can be moved toward the optical axis so as to deliver illumination light deep into the root canal Sa. In this case, the driving sections 73 only need to operate based on the magnification and may operate manually or automatically, for example. When the image magnification is small, the light-reception area is large.

As illustrated in FIG. 2, the controller 8 includes the drive control unit 83 controlling the driving sections 73.

By automatically controlling the driving sections 73, the drive control unit 83 easily changes the arrangement of the light emitting elements 61 to 64 of the illumination units 6.

As illustrated in FIG. 2, the controller 8 includes the irradiation angle control unit 84 to control the irradiation angle θ2 (see FIGS. 10B and 11B) of the illumination units 6. The irradiation angle control unit 84 controls the irradiation angle θ2 based on the magnification.

By changing the irradiation angle θ2, the irradiation angle control unit 84 allows for emission of brighter illumination light toward the root canal Sa, thus improving the visibility within the root canal Sa.

As illustrated in FIG. 9 or 10B, the plurality of illumination units 6 are provided, and at least two of the plurality of illumination units 6 emit illumination light beams intersecting on the irradiation area.

In the plurality of illumination units 6, the inclination angle θ1 of the optical axes 6a are adjusted so that the illumination light beams intersect at a predetermined position on the optical axis Ax of the imaging section 7, thus providing a shadowless effect (higher illuminance).

[First Modification]

The present invention is not limited to the aforementioned embodiment and can be variously modified and changed within the scope of the technical idea thereof. It is certain that the present invention includes these modified or changed inventions.

Figure 16A:
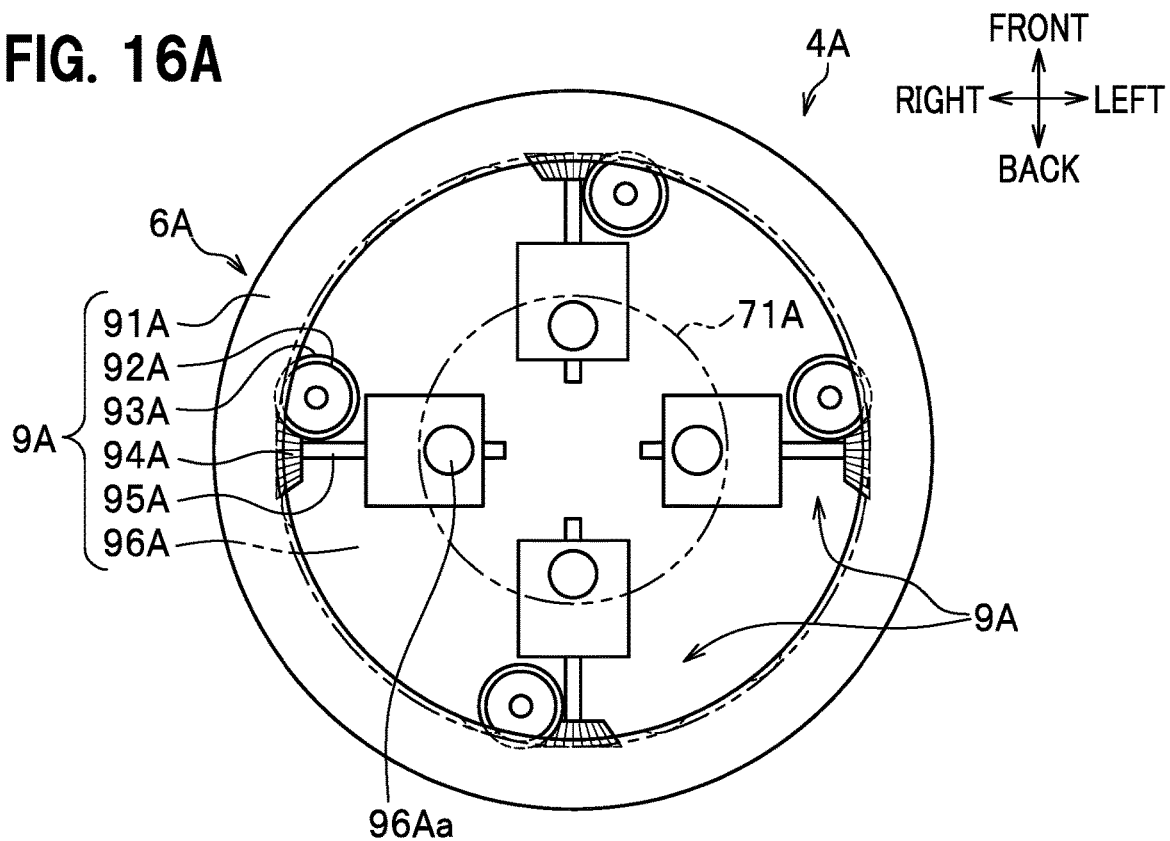
FIGS. 16A and 16B are views illustrating a first modification of the medical optical imaging device according to the embodiment of the present invention, FIG. 16A being a schematic perspective view illustrating the structure of the illumination units, FIG. 16B being a schematic side view illustrating the structure of the illumination units.
Figure 16B:
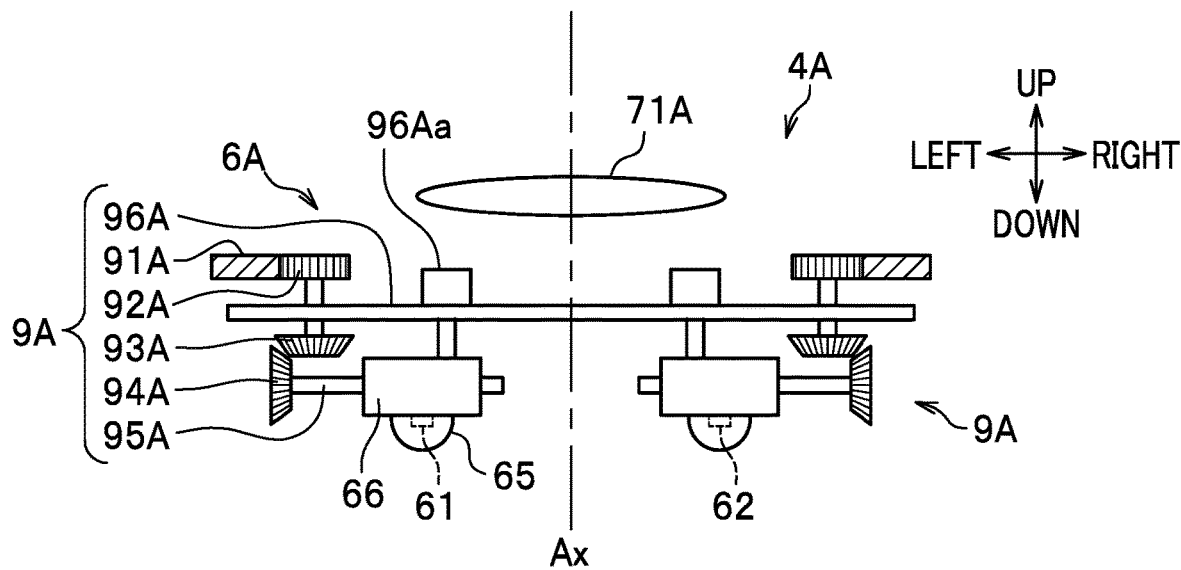

FIGS. 16A and 16B are views illustrating a first modification of the medical optical imaging device according to the embodiment of the present invention, FIG. 16A being a schematic perspective view illustrating the structure of the illumination units, FIG. 16B being a schematic side view illustrating the structure of the illumination units.

The driving mechanism of the aforementioned embodiment illustrated in FIG. 9, which include the electric motors 691 that move the light emitting elements 61 to 64, the male thread members 692, and the female thread members 693, may be illumination unit driving mechanisms 9A including a gear mechanism illustrated in FIGS. 16A and 16B.

Each illumination unit driving mechanism 9A includes a first gear 91A driven by an electric motor (not illustrated), a second gear 92A, a third gear 93A, a fourth gear 94A, a thread member 95A, and a support member 96A.

The first gear 91A is an internal gear which is located to surround the four illumination unit driving mechanisms 9A on the front, back, left, and right sides and is engaged with the four second gears 92A on the front, back, left, and right sides to drive the same.

The second gears 92A are spur gears rotationally driven by the first gear 91A.

The third gears 93A are bevel gears provided coaxially and rotated integrally with the corresponding second gears 92A. The shafts coupling the second and third gears 92A and 93A are axially supported by the support member 96A so as to freely rotate.

The fourth gears 94A are bevel gears engaged with the third gears 93A to be rotated.

The thread members 95A are composed of ball screws each having the proximal end fixed to the corresponding fourth gear 94A to be rotated integrally and having the distal end engaged with the corresponding female thread member 693 (see FIG. 9) provided for the corresponding light-source mounted table 66. The ball screws thereby reciprocate the respective light-source mounted tables 66.

The support member 96A is a plate member supporting the illumination unit driving mechanisms 9A and light-source mounted tables 66.

The light-source mounted tables 66 are held on the support member 96A with light-source mounted table support members 96Aa.

The thus-configured first modification provides the same operation effects as the aforementioned embodiment.

[Second Modification]

FIGS. 17A and 17B are views illustrating a second modification as a medical optical imaging device 4B according to the embodiment of the present invention, FIG. 17A being an explanatory view illustrating the state of illumination units 6B for a smaller magnification, FIG. 17B being an explanatory view illustrating the state of the illumination units 6B for a larger magnification.

The driving sections 73 tilting the illumination units 6 illustrated in FIGS. 12A and 12B in the aforementioned embodiment may be driving sections 73B each including: an energizing member 73Bd pressing the distal end of an illumination unit tilting section 73Bb; and a limiting member 73Be limiting movement of the illumination unit tilting section 73Bb pressed by the energizing member 73Bd as illustrated in FIGS. 17A and 17B.

In this case, an end on the optical axis Ax side of a fixed section 73Ba fixed to the corresponding light-source mounted table 66 and an end on the optical axis Ax side of the illumination unit tilting section 73Bb are coupled with a hinge member 73Bc.

The energizing member 73Bd is a member pressing the illumination unit tilting section 73Bb toward the illumination unit 6 to tilt the illumination unit tilting section 73Bb with the illumination unit 6 mounted thereon, about the hinge member 73Bc. The energizing member 73Bd is composed of a spring member, such as a plate spring or a torsion spring, or a pressing member.

The limiting member 73Be is a stopper supporting the illumination unit tilting section 73Bb tilted toward the illumination unit 6 side by the energizing member 73Bd so that the illumination unit tilting section 73Bb is stopped at a desired position. The limiting member 73Be is located at the other end of the illumination unit tilting section 73Bb on the illumination unit 6 side.

The driving section 73B thus provides the same operation effects as those of the driving section 73 of the aforementioned embodiment.

[Third Modification]

Figure 18:
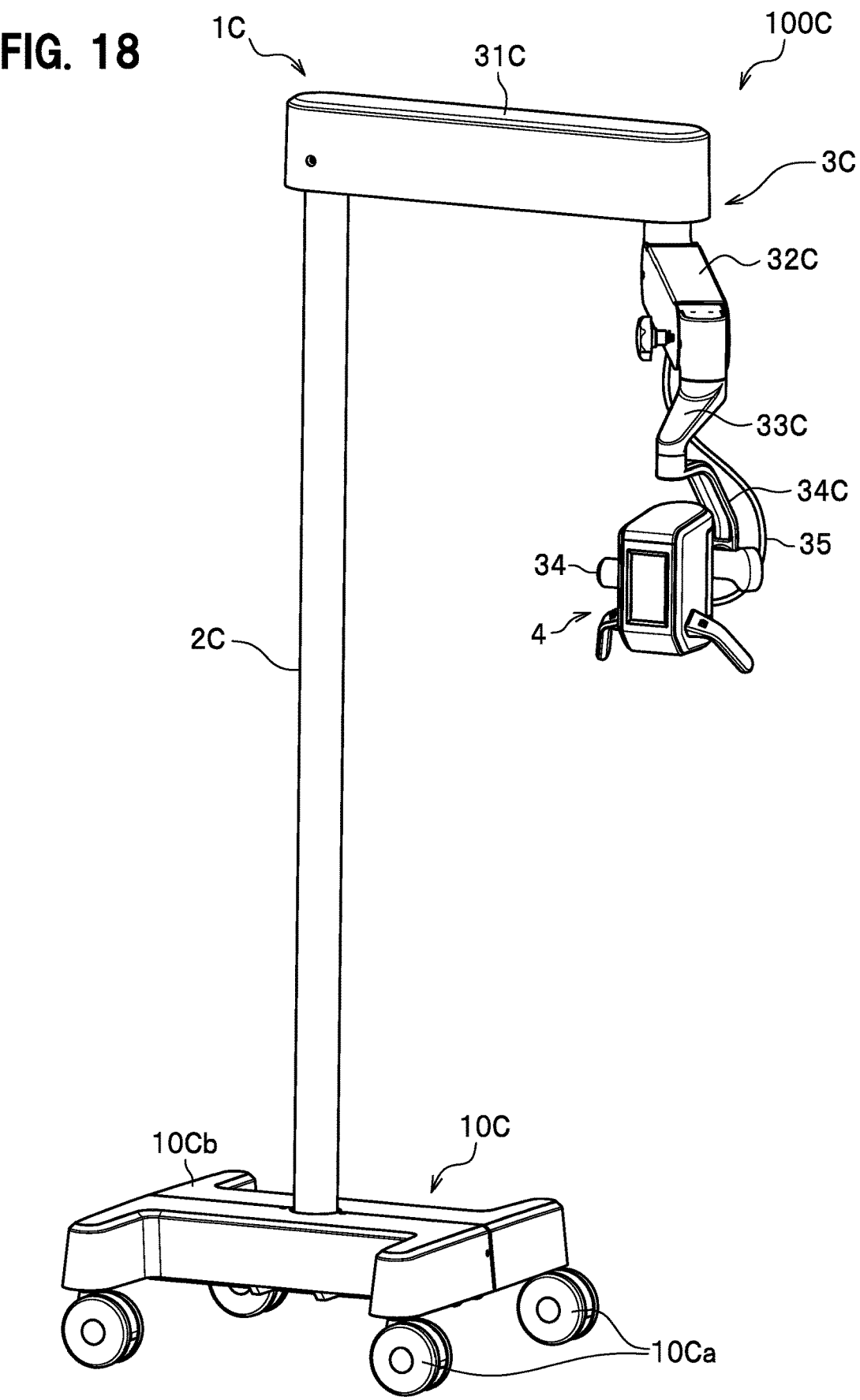
FIG. 18 is a perspective view illustrating a third modification of the medical examination apparatus according to the embodiment of the present invention.

FIG. 18 is a perspective view illustrating a third modification as a medical examination apparatus 100C.

In the medical examination apparatus 100 described in the above embodiment, the medical optical imaging device 4 is mounted on the tip of the arm 3 of the dental treatment unit 1. As illustrated in FIG. 18, the imaging device 4 may be mounted on the tip of an arm 3C of an imaging device stand 1C.

In this case, the stand 1C includes a base 10C, a support column 2C stood on the base 10C, and the arm 3C axially supported on the top of the support column 2C. On the tip of the arm 3C provided at the top of the stand 1C, the imaging device 4 is replaceably mounted. The stand 1C allows the imaging device 4 to be mounted thereon.

The base 10C includes a plurality of casters 10Ca and a base body 10Cb supporting the plurality of casters 10Ca.

The casters 10Ca are composed of commercially-available casters with stoppers which are screwed to the bottom of the base body 10Cb at four places on the right and left in the front and back sides.

The base body 10Cb is composed of a metallic frame including a pair of right and left transverse frames and a longitudinal frame laid in the center of the pair of transverse frames, for example.

The support column 2C is a column member rotatably supporting the proximal end of the arm 3C. The support column 2C is stood in the center of the base body 10Cb having a substantially H-shape in a plan view. The support column 2C is composed of a metallic cylindrical member through which the harness 35 electrically connecting the imaging device 4 to a power supply and the like is inserted, for example.

The arm 3C is composed of a balance arm arranged to extend from the support column 2C to the imaging device 4. The balance arm includes supporting power to elastically support the imaging device 4 so as to move the imaging device 4 up, down, left, right, forward, and backward by applying a force not less than a predetermined force in the direction of movement. The arm 3C, for example, includes a first arm 31C provided on the top of the support column 2C; a second arm 32C, a third arm 33C, and a fourth arm 34C sequentially arranged on the distal end side of the first arm 31C; and an attachment member 34 which is provided on the fourth arm 34C and detachably couples the imaging device 4 to the fourth arm 34C. In the arm 3C (the first and second arms 31C and 32C, for example), the harness 35 is laid with the proximal end inserted in the support column 2C and the distal end to be connected to a connector (not illustrated) provided for the housing 41 of the imaging device 4.

The imaging device 4 therefore can be mounted for use on the tip of the arm 3C of the stand 1C which is used in dental treatments, examinations, surgeries, and the like.

[Fourth Modification]

In the aforementioned embodiment, the illumination units 6 are prevented from producing mechanical vignetting by setting the imaging lens system 71 to the telephoto imaging (high-magnification) position with the wide-angle range A being small and moving the illumination units 6 closely within the range where the illumination units 6 do not block the imaging optical path R1 of the imaging element 72. However, the present invention is not limited to such a configuration.

For example, it is possible to prevent occurrence of mechanical vignetting by detecting the positional information of the imaging lens system 71 (mainly the zoom lens) and thereby preventing the imaging lens from moving to such a position that mechanical vignetting can occur.

Furthermore, even if the illumination units 6 are located within the angle of view, image processing can be executed so as to display image part including no mechanical vignetting, thus displaying an image free of mechanical vignetting.

[Other Modifications]

In the description of the aforementioned embodiment and the third modification, as an installation example of the imaging device 4, the imaging device 4 is mounted on the tip of the arm 3 of the dental treatment unit 1 (see FIG. 1) or is mounted on the tip of the arm 3C of the stand 1C (see FIG. 18). However, the present invention is not limited to these configurations.

For example, the imaging device 4 may be mounted on a ceiling-mounted arm which is provided on the ceiling of a dental treatment room, a floor-mounted arm which is provided on the floor of a dental treatment room, a stand-type arm which is provided on a table, such as a dental treatment table, or the like.

In the embodiment, the imaging device 4 composed of an optical camera, digital camera, a digital microscope, and the like is described as an example of the medical examination apparatus 100 by way of example. In addition, an optical microscope is also applicable. The medical examination apparatus 100 which employs an optical microscope also provides a small-sized, inexpensive apparatus capable of illuminating even deep part of a root canal with the illumination units 6.

REFERENCE SIGNS LIST

4 IMAGING DEVICE (MEDICAL OPTICAL IMAGING DEVICE)
5 DISPLAY SECTION
6 ILLUMINATION UNIT
6a OPTICAL AXIS
6b INTERSECTION
7 IMAGING SECTION
8 CONTROLLER
43 GRIP SECTION
61 TO 64 LIGHT EMITTING ELEMENT
71 IMAGING LENS SYSTEM
71a SENSOR LIGHT-RECEPTION AREA (LIGHT RECEPTION SURFACE)
72 IMAGING ELEMENT
73 DRIVING SECTION
81 DISPLAY CONTROL UNIT
82 MAGNIFICATION CHANGE UNIT
83 DRIVE CONTROL UNIT
84 IRRADIATION ANGLE CONTROL UNIT
100 MEDICAL EXAMINATION APPARATUS
L1 IMAGING DISTANCE FROM IMAGING SECTION TO SUBJECT
R1 IMAGING OPTICAL PATH
S SUBJECT
Sa ROOT CANAL
Sb OPENING
θ1 ACUTE ANGLE
θ2 IRRADIATION ANGLE

The invention claimed is:

1. A medical optical imaging device comprising:
    at least one illumination unit which emits illumination light toward a subject;
    an imaging section which images the subject; and
    a controller which controls at least the imaging section, wherein
    the imaging section includes an imaging lens system and an imaging element receiving an optical image formed by the imaging lens system,
    the illumination unit is located in front of the imaging lens system to overlap the imaging lens system as viewed from the subject's side, and
    the illumination unit has an illuminance of not less than 7500 Lx around the subject when an imaging distance from the imaging section to the subject is 300 to 500 mm.

2. The medical optical imaging device according to claim 1, wherein
    the illumination unit is composed of a plurality of light emitting elements irradiating the subject,
    the subject is a root canal, and
    optical axes of the light emitting elements are arranged to intersect at an acute angle after the optical axes pass through an opening of the root canal.

3. The medical optical imaging device according to claim 2, wherein
    the imaging section includes an autofocus function, and
    an intersection in which the optical axes intersect at an acute angle is located in a focal range of the imaging lens system by the autofocus function.

4. The medical optical imaging device according to claim 3, further comprising
    a grip section configured to operate the illumination unit and/or the imaging section, wherein
    the grip section includes a switch section to execute the autofocus function.

5. The medical optical imaging device according to claim 2, wherein
    a focus of the imaging section is fixed focus, and
    the fixed focus is located in the intersection in which the optical axes intersect at an acute angle.

6. The medical optical imaging device according to claim 2, wherein one of the plurality of light emitting elements emits light with a peak wavelength of 380 to 500 nm.

7. The medical optical imaging device according to claim 1, wherein the illumination unit is located in a range where the illumination unit does not block an imaging optical path to the imaging element.

8. The medical optical imaging device according to claim 1, wherein
    the controller includes a display control unit to display a captured image on a display section, and
    the display control unit performs at least one of moving the imaging lens system and executing image processing for imaging data acquired from the imaging element such that the illumination unit is not displayed when the illumination unit blocks an imaging optical path to the imaging element, and displays the captured image on the display section.

9. A medical optical imaging device comprising:
    at least one illumination unit which emits illumination light toward a subject
    an imaging section which images the subject and
    a controller which controls at least the imaging section, wherein
    the imaging section includes an imaging lens system and an imaging element receiving an optical image formed by the imaging lens system,
    the illumination unit is located in front of the imaging lens system to overlap the imaging lens system as viewed from the subject's side, and
    the illumination unit is arranged such that the aspect ratio of a light reception surface of the imaging lens system is equal to the aspect ratio of the display size on a display section, of an image captured by the imaging section.

10. The medical optical imaging device according to claim 9, wherein
    the controller includes a magnification change unit changing the magnification for an image to be captured by the imaging section,
    the imaging section includes a driving section to change the arrangement of the illumination unit, and
    the magnification change unit changes the magnification by at least one of moving the imaging lens system and executing image processing for imaging data acquired by the imaging element, and
    the driving section is operated based on the magnification.

11. The medical optical imaging device according to claim 10, wherein the controller includes a drive control unit controlling the driving section.

12. The medical optical imaging device according to claim 10, wherein
    the controller includes an irradiation angle control unit to control an irradiation angle of the illumination unit, and
    the irradiation angle control unit controls the irradiation angle based on the magnification.

13. The medical optical imaging device according to claim 2, wherein
    a plurality of illumination units are arranged, and illumination light beams from at least two of the plurality of illumination units intersect on an irradiation area.

* * * * *